United States Patent
Apte et al.

(10) Patent No.: US 10,169,541 B2
(45) Date of Patent: *Jan. 1, 2019

(54) METHOD AND SYSTEMS FOR CHARACTERIZING SKIN RELATED CONDITIONS

(71) Applicant: uBiome, Inc., San Francisco, CA (US)

(72) Inventors: Zachary Apte, San Francisco, CA (US); Jessica Richman, San Francisco, CA (US); Catalina Valdivia, San Francisco, CA (US); Daniel Almonacid, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/497,072

(22) Filed: Apr. 25, 2017

(65) Prior Publication Data

US 2017/0228514 A1 Aug. 10, 2017

Related U.S. Application Data

(63) Continuation-in-part of application No. 15/098,153, filed on Apr. 13, 2016, which is a continuation-in-part of application No. 14/919,614, filed on Oct. 21, 2015, now Pat. No. 9,703,929.

(60) Provisional application No. 62/146,789, filed on Apr. 13, 2015, provisional application No. 62/147,083, filed on Apr. 14, 2015, provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015, provisional application No. 62/327,048, filed on Apr. 25, 2016, provisional application No. 62/327,089, filed on Apr. 25, 2016, provisional application No. 62/327,126, filed on Apr. 25, 2016.

(51) Int. Cl.

| | |
|---|---|
| *G01N 33/48* | (2006.01) |
| *G06F 19/00* | (2018.01) |
| *G06F 19/24* | (2011.01) |
| *G06F 19/28* | (2011.01) |
| *C12Q 1/6874* | (2018.01) |
| *G16H 50/20* | (2018.01) |
| *G06G 7/58* | (2006.01) |

(52) U.S. Cl.
CPC ....... *G06F 19/3418* (2013.01); *C12Q 1/6874* (2013.01); *G06F 19/24* (2013.01); *G06F 19/28* (2013.01); *G06F 19/345* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 6,033,864 A | 3/2000 | Braun et al. | |
| 6,309,643 B1 | 10/2001 | Braun et al. | |
| 6,632,641 B1 | 10/2003 | Brennan et al. | |
| 6,861,053 B1 | 3/2005 | Lin et al. | |
| D521,843 S | 5/2006 | Hung | |
| 7,048,906 B2 | 5/2006 | Lin et al. | |
| 7,176,002 B2 | 2/2007 | Lao et al. | |
| 8,478,544 B2 | 7/2013 | Colwell et al. | |
| 8,598,203 B2 | 12/2013 | Tarcic et al. | |
| 9,028,841 B2 | 5/2015 | Henn et al. | |
| 9,149,473 B2 | 10/2015 | Ecker et al. | |

(Continued)

FOREIGN PATENT DOCUMENTS

| | | |
|---|---|---|
| CN | 105407728 | 3/2016 |
| EP | 2631240 | 8/2013 |

(Continued)

OTHER PUBLICATIONS

"K03100: IepB: signal pepidase I," KEGG, Aug. 7, 2012 (Aug. 7, 2012), p. 1 of 1. Retrieved from the Internet: on Jun. 12, 2016 (Jun. 12, 2016).

(Continued)

*Primary Examiner* — Eric S DeJong
(74) *Attorney, Agent, or Firm* — Kilpatrick Townsend & Stockton LLP

(57) ABSTRACT

Embodiments of a method and system for characterizing a skin-related condition in relation to a user can include one or more of: a handling network operable to collect containers comprising material from a set of users, the handling network comprising a sequencing system operable to determine microorganism sequences from sequencing the material; a microbiome characterization system operable to: determine at least one of microbiome composition data and microbiome functional diversity data based on the microorganism sequences, collect supplementary data associated with the skin-related condition for the set of users, and transform the supplementary data and the at least one of the microbiome composition data and the microbiome functional diversity data into a characterization model; and a therapy system operable to promote a treatment to the user for the skin-related condition based on characterizing the user with the characterization model in relation to the skin-related condition.

30 Claims, 13 Drawing Sheets

(56) References Cited

U.S. PATENT DOCUMENTS

| | | |
|---|---|---|
| 9,433,651 B2 | 9/2016 | Jones et al. |
| 9,506,109 B2 | 11/2016 | Savelkoul et al. |
| 9,663,831 B2 | 5/2017 | Apte et al. |
| 2002/0012926 A1 | 1/2002 | Quake et al. |
| 2003/0190314 A1 | 10/2003 | Campbell et al. |
| 2005/0196785 A1 | 9/2005 | Quake et al. |
| 2006/0089310 A1 | 4/2006 | Goldstein et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0172874 A1 | 7/2010 | Turnbaugh et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0189621 A1 | 7/2012 | Dean et al. |
| 2012/0252775 A1 | 10/2012 | Finegold |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0242080 A1 | 8/2014 | Jaeger et al. |
| 2014/0315929 A1 | 10/2014 | Chiosis |
| 2014/0341853 A1 | 11/2014 | Hovanky |
| 2014/0377270 A1 | 12/2014 | Moore et al. |
| 2015/0050245 A1 | 2/2015 | Herman et al. |
| 2015/0056206 A1 | 2/2015 | Zhou |
| 2016/0017058 A1 | 1/2016 | Kim et al. |
| 2016/0040216 A1 | 2/2016 | Akins et al. |
| 2016/0271189 A1 | 9/2016 | Cutcliffe et al. |

FOREIGN PATENT DOCUMENTS

| | | |
|---|---|---|
| WO | 050513 | 4/2012 |
| WO | 142378 | 9/2013 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 085326 | 6/2015 |
| WO | 095241 | 6/2015 |
| WO | 103165 | 7/2015 |
| WO | 170979 | 11/2015 |
| WO | 138337 | 9/2016 |
| WO | 172643 | 10/2016 |

OTHER PUBLICATIONS

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016 (Jun. 20.

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Apr. 1, 2012), vol. 13, pp. 260-270.

Greenblum et al. "Metagenomic Systems and Biology of the Human Gut Microbiome Reveals Topological Shifts Associated with Obesity and Inflammatory Bowel Disease," Proceeding of the National Academy of Sciences, Jan. 10, 2012 (Dec. 19, 2012), vol. 109, Pgs.

Kanehisa et al. "KEGG: Kyoto encyclopedia of genes and genomes," Nucleic Acids Research, Jan. 1, 2000 (Jan. 1, 2000), vol. 28, No.1, pp. 27-30.

Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.

Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.

Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.

Ponnusamy et al. "Microbial community and metabolomic comparison of irritable bowel syndrome faeces," Feb. 17, 2011 (Feb. 17, 2011), vol. 60, pp. 817-827. entire document.

Non-Final Office Action dated Jul. 12, 2018 in U.S. Appl. No. 15/098,153, filed Apr. 13, 2016. 14 pages.

block pathogen entry form mucous barrier enhance apical tight junctions produce antimicrobial factors stimulate anti-inflammatory cytokines

METHOD AND SYSTEMS FOR CHARACTERIZING SKIN RELATED CONDITIONS

CROSS-REFERENCE TO RELATED APPLICATIONS

This application is a continuation-in-part of U.S. patent application Ser. No. 15/098,153, filed 13 Apr. 2016, which claims the benefit of U.S. Provisional Application Ser. No. 62/146,789, filed 13 Apr. 2015 and U.S. Provisional Application Ser. No. 62/147,083, filed 14 Apr. 2015, and is a continuation-in-part of U.S. patent application Ser. No. 14/919,614, filed 21 Oct. 2015, which claims the benefit of U.S. Provisional Application Ser. No. 62/066,369, filed 21 Oct. 2014, U.S. Provisional Application Ser. No. 62/087,551, filed 4 Dec. 2014, U.S. Provisional Application Ser. No. 62/092,999, filed 17 Dec. 2014, U.S. Provisional Application Ser. No. 62/147,376, filed 14 Apr. 2015, U.S. Provisional Application Ser. No. 62/147,212, filed 14 Apr. 2015, U.S. Provisional Application Ser. No. 62/147,362, filed 14 Apr. 2015, U.S. Provisional Application Ser. No. 62/146,855, filed 13 Apr. 2015, and U.S. Provisional Application Ser. No. 62/206,654, filed 18 Aug. 2015, which are each incorporated in its entirety herein by this reference.

This application additionally claims the benefit of U.S. Provisional Application Ser. No. 62/327,048, filed 25 Apr. 2016, U.S. Provisional Application Ser. No. 62/327,089, filed 25 Apr. 2016, and U.S. Provisional Application Ser. No. 62/327,126, filed 25 Apr. 2016, which are each incorporated in their entirety by this reference.

TECHNICAL FIELD

This invention relates generally to the field of microbiology and more specifically to a new and useful method and system for characterizing skin-related conditions in the field of microbiology.

BACKGROUND

A microbiome is an ecological community of commensal, symbiotic, and pathogenic microorganisms that are associated with an organism. The human microbiome includes over to times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, autoimmune disorders, gastrointestinal disorders, rheumatoid disorders, neurological disorders, etc.). Given the profound implications of the microbiome in affecting a user's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific users based upon microbiome composition and/or functional features have not been viable due to limitations in current technologies.

As such, there is a need in the field of microbiology for a new and useful method and system for characterizing health conditions in an individualized and population-wide manner. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview.

Figure 2:
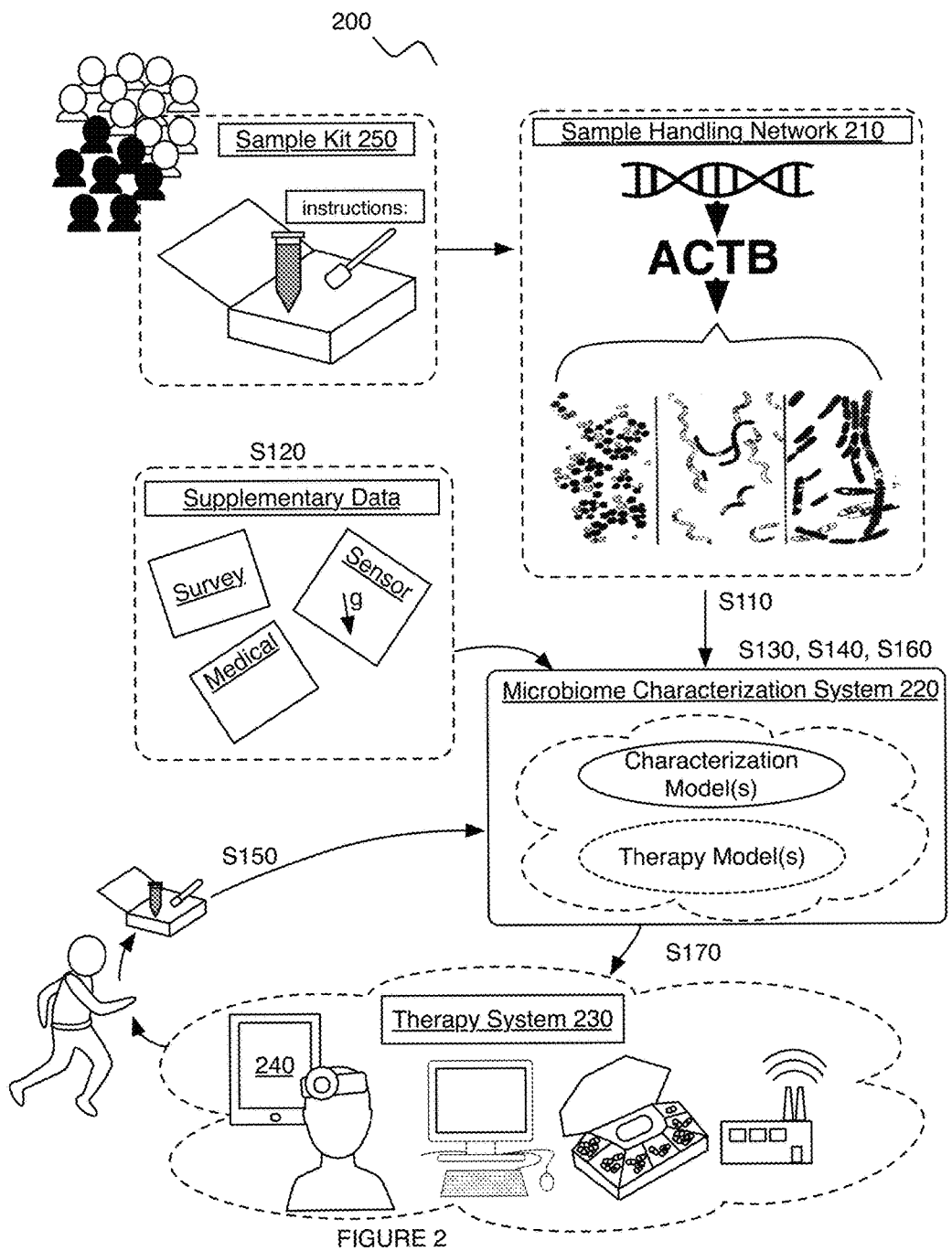
FIG. 2 depicts variations of embodiments of a system and method for microbiome characterization.

As shown in FIG. 2, embodiments of a system 200 for characterizing (e.g., evaluating) a skin-related condition in relation to a user (e.g., a human subject, an animal subject, etc.) can include one or more of: a handling network 210 operable to collect containers including material from a set of users (e.g., a population of users), the handling network 210 including a sequencing system operable to determine microorganism sequences from sequencing the material; a microbiome characterization system 220 operable to: determine at least one of microbiome composition data and microbiome functional diversity data based on the microorganism sequences, collect supplementary data associated with the skin-related condition for the set of users, and transform the supplementary data and features extracted from the at least one of the microbiome composition data and the microbiome functional diversity data into a characterization model for the skin-related condition; and a therapy system 230 (e.g., treatment system) operable to promote a treatment to the user for the skin-related condition based on characterizing the user with the characterization model in relation to the skin-related condition.

The system 200 and method 100 can function to generate models that can be used to characterize and/or diagnose users according to at least one of their microbiome composition and functional features (e.g., as a clinical diagnostic, as a companion diagnostic, etc.); provide therapeutic measures (e.g., probiotic-based therapeutic measures, phage-based therapeutic measures, small-molecule-based therapeutic measures, clinical measures, etc.) to users based upon microbiome analysis for a population of users; and/or perform any suitable function.

The system 200 and method 100 can preferably generate and promote characterizations and therapies for skin-related conditions, which can include any one or more of skin-related: symptoms, causes, diseases, disorders, and/or any other suitable aspects associated with skin-related conditions. Skin-related conditions can include any one or more of: eczema (e.g., atopic dermatitis, allergic contact dermatitis, irritant contact dermatitis, stasis dermatitis, acrodermatitis, seborrhoeic eczema, xerotic eczema, dyshidrosis, discoid eczema, venous eczema, dermatitis herpetiformis, neurodermatitis, autoeczematization, eczema herpeticum, etc.), dry skin, a scalp-related condition (e.g., dandruff, hair loss, cradle cap, scalp-related, head lice, ringworm, folliculitis, scalp psoriasis, etc.), photosensitivity (e.g., photoallergy, phototoxicity, etc.), a pimple-related condition (e.g., pimples, papules, nodules, epidermoid cysts, sebaceous cysts, pilonidal cyst, other cysts, pilonidal abscess, pustules, blackheads, whiteheads, acne-associated pus, other acne-associated conditions, etc.), rosacea, oily skin, skin cancer, lupus, rubeola, psoriasis, cold sores, hemangioma, hives, shingles, pemphigoid, tinea versicolor, corns, calluses, ulcers (e.g., decubitus ulcers, leg ulcers, etc.), keloid, lichen planus, actinic keratosis, pilonidal sinus, seborrheic keratosis, ingrown nails, ingrown hairs, canker sores, herpes stomatitis, fungal nail infection, ichthyosis vulgaris, dermatomyositis, molluscum contagiosum, cutis laxa, erysipelas, rash (e.g., diaper rash), dyshidrotic eczema, canker sores, impetigo, necrotizing fasciitis, cutaneous candidiasis, carbuncle, cellulitis, hypohidrosis, hyperhidrosis, warts (e.g., plantar warts, palmer warts, etc.), blisters, chafing, sunburn, Muehrcke's lines, varicose veins, lice, scabies, plant-related skin-related conditions (e.g., rashes associated with poison ivy, oak, sumac, etc.), bruises, bedbug-associated conditions, lumps, itching, vitiligo, leprosy, boils, staph infection, athlete's foot, sporotrichosis, fungal nail infection, shingles, chickenpox, other bacterial skin infections, other fungal skin infections, and/or any other suitable skin-related conditions.

One or more instances of the method 100 and/or processes described herein can be performed asynchronously (e.g., sequentially), concurrently (e.g., in parallel; concurrently on different threads for parallel computing to improve system processing ability for determining and/or providing characterizations and/or therapies for skin-related conditions; etc.), in temporal relation to a trigger event, and/or in any other suitable order at any suitable time and frequency by and/or using one or more instances of the system 200, elements, and/or entities described herein. However, the method 100 and/or system 200 can be configured in any suitable manner.

2. Benefits

Microbiome analysis can enable accurate and efficient characterization and/or therapy provision for skin-related conditions caused by and/or otherwise associated with microorganisms. The technology can overcome several challenges faced by conventional approaches in characterizing and/or promoting therapies for skin-related conditions. First, conventional approaches can require patients to visit a care provider who performs a physical inspection in relation to skin-related conditions. Second, conventional genetic sequencing and analysis technologies for human genome sequencing can be incompatible and/or inefficient when applied to the microbiome (e.g., where the human microbiome can include over to times more microbial cells than human cells; where optimal sample processing techniques can differ; where sequence reference databases can differ; where microbiome characterization can include accounting for the different compositions and functional diversity of the microbiome across populations; where the microbiome can vary across different body regions of the user; etc.). Third, the onset of sequencing technologies (e.g., next-generation sequencing) has given rise to technological issues (e.g., data processing issues, information display issues, microbiome analysis issues, therapy prediction issues, therapy provision issues, etc.) that would not exist but for the unprecedented advances in speed and data generation associated with sequencing genetic material. Examples of the system 200 and the method 100 can confer technologically-rooted solutions to at least the challenges described above.

First, the technology can confer improvements in computer-related technology (e.g., artificial intelligence, machine learning, biological sample processing and computational analysis network, etc.) by facilitating computer performance of functions not previously performable. For example, the technology can computationally generate microbiome characterizations and recommended therapies for skin-related conditions, based on microbiome sequence datasets and microorganism reference sequence databases (e.g., Genome Reference Consortium) that are recently viable due to advances in sample processing techniques and sequencing technology.

Second, the technology can confer improvements in processing speed, microbiome characterization accuracy, microbiome-related therapy determination and promotion, and/or other suitable aspects in relation to skin-related conditions. The technology can generate and apply skin-related feature-selection rules to select an optimized subset of features (e.g., microbiome composition features, microbiome functional diversity features, etc.) out of a vast potential pool of features (e.g., extractable from the plethora of microbiome data) for generating and applying characterization models and/or therapy models. The potential size of microbiomes (e.g., human microbiomes, animal microbiomes, etc.) can translate into a plethora of data, giving rise to questions of how to process and analyze the vast array of data to generate actionable microbiome insights in relation to skin-related conditions. However, the skin-related feature-selection rules and associated technology can enable shorter training and execution times (e.g., for predictive machine learning models), model simplification facilitating efficient interpretation of results, reduction in overfitting, improvements in data sources (e.g., for collecting and processing microbiome datasets), improvements in identifying and presenting skin-related condition insights in relation to the microbiome, and other suitable improvements to facilitate rapid determination of characterizations and/or therapies.

Third, the technology can transform entities (e.g., users, biological samples, therapy systems including medical devices, etc.) into different states or things. For example, the system 200 and/or method 100 can identify therapies to promote to a patient to modify microbiome composition and/or function to prevent and/or ameliorate skin-related conditions, thereby transforming the microbiome and/or health of the patient. In another example, the technology can transform biological samples (e.g., through fragmentation, multiplex amplification, sequencing, etc.) received by patients into microbiome datasets, which can subsequently be transformed into features correlated with skin-related conditions, in order to generate characterization models and/or therapy models. In another example, the technology can control therapy systems to promote therapies (e.g., by generating control instructions for the therapy system to execute), thereby transforming the therapy system. In another example, the improvements in computer-related technology can drive transformations in the biological sample processing approaches, such as selecting a subset of primers compatible with genetic targets identified to correspond to microbiome composition features and/or microbiome functional diversity features correlated (e.g., determined based on skin-related feature selection rules) with skin-related conditions.

Fourth, the technology can amount to an inventive distribution of functionality across a network including a sample handling network, microbiome characterization system, and a plurality of users, where the sample handling network can handle simultaneous processing of biological samples (e.g., in a multiplex manner) from the plurality of users, which can be leveraged by the microbiome characterization system in generating user-personalized characterizations and/or therapies (e.g., customized to the user's microbiome, medical history, demographics, behaviors, preferences, etc.) for skin-related conditions.

Fifth, the technology can improve the technical fields of at least computational modeling of skin-related conditions in relation to microbiome digital medicine, digital medicine, genetic sequencing, and/or other relevant fields. Sixth, the technology can leverage specialized computing devices (e.g., devices associated with the sample handling network, such as sequencing systems; microbiome characterization systems; treatment systems; etc.) in determining and processing microbiome datasets for characterizing and/or determining therapies for skin-related conditions. The technology can, however, provide any other suitable benefit(s) in the context of using non-generalized computer systems for microbiome characterization and/or modulation.

3. System.

The handling network 210 of the system 200 can function to receive and process (e.g., fragment, amplify, sequence, etc.) biological samples. The handling network 210 can additionally or alternatively function to provide and/or collect sample kits 250 (e.g., including sample containers, instructions for collecting samples, etc.) for a plurality of users (e.g., in response to a purchase order for a sample kit 250), such as through a mail delivery system. In examples, the sample kits 250 can include materials and associated instructions for a user to collect a skin sample (e.g., through cotton tip swabs; aspiration of skin-related fluids such as fluids from a skin lesion; biopsy; etc.). The handling network 210 can additionally or alternatively include a library preparation system operable to automatically prepare biological samples (e.g., fragment and amplify using primers compatible with genetic targets associated with the skin-related condition) in a multiplex manner to be sequenced by a sequencing system; and/or any suitable components. However, the handling network 210 and associated components can be configured in any suitable manner.

The microbiome characterization system 220 of the system 200 can function to determine and analyze microbiome datasets and/or supplementary datasets for characterizing and/or determining therapies for skin-related conditions. In a variation, the microbiome characterization system 220 can obtain and/or apply computer-implemented rules (e.g., skin-related feature selection rules; model generation rules; user preference rules; microorganism sequence generation rules; sequence alignment rules; and/or any other suitable rules). However, the microbiome characterization system 220 can be configured in any suitable manner.

The therapy system 230 of the system 200 functions to promote one or more therapies to a user (e.g., subject; care provider administering the therapy; etc.) for treating a skin-related condition (e.g., reducing the risk of a skin-related infection, etc.). The therapy system 230 can include any one or more of: a communications system (e.g., to communicate therapy recommendations; to enable telemedicine; etc.; etc.), an application executable on a user device (e.g., a skin-related condition application for promoting proper skincare therapies operable to modify microbiome composition and/or functional diversity in relation to skin-related conditions, etc.), skin-related therapies (e.g., treatments), supplementary medical devices (e.g., medication dispensers; skin treatment applicators; skin grafting devices; radiofrequency-based skin-related devices; hair-related condition devices such as hair restoration devices, hair removal devices; acne-related medical devices; other diagnostic devices such as cutaneous hydration measurement devices; other treatment devices; etc.), user devices (e.g., including biometric sensors), and/or any other suitable component.

One or more therapy systems 230 are preferably controllable by the microbiome characterization system 220. For example, the microbiome characterization system 220 can generate control instructions and/or notifications to transmit to the therapy system 230 for activating and/or otherwise operating the therapy system 230 in promoting the therapy. However, the therapy system 230 can be configured in any other manner.

Figure 9:
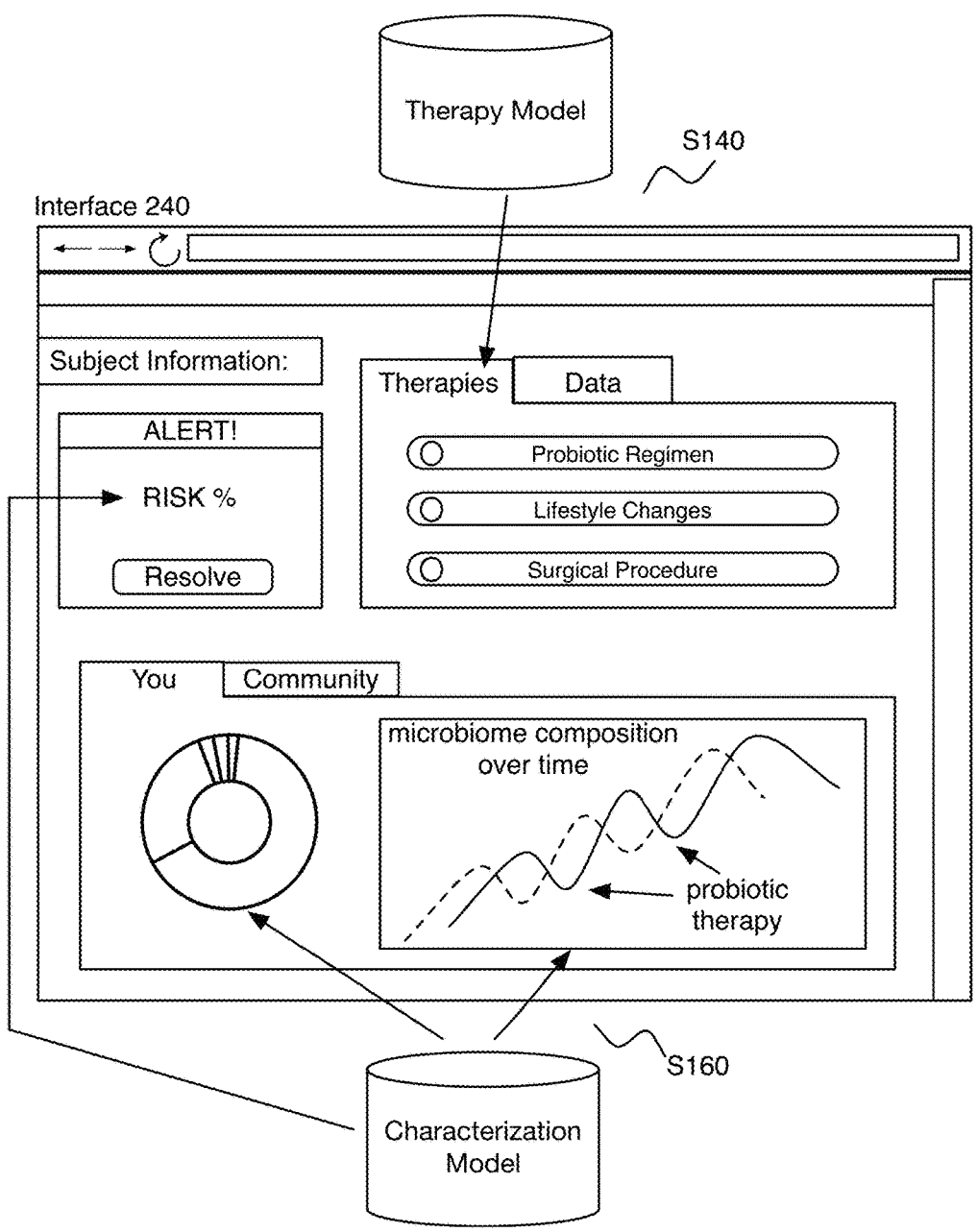
FIG. 9 depicts a variation of an interface for providing skin-related condition information in an embodiment of a method for microbiome characterization.
Figure 11:
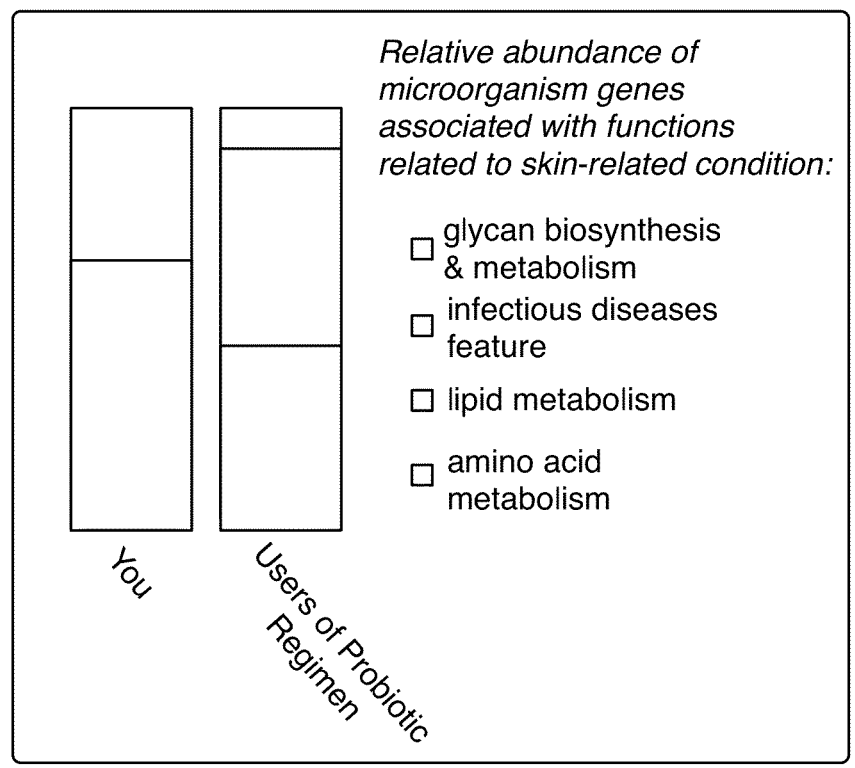
FIG. 11 depicts a variation of notification provision in an embodiment of a method for microbiome characterization.

As shown in FIG. 9, the system 200 can additionally or alternatively include an interface 240 that can function to improve presentation of skin-related condition information (e.g., characterizations; therapy recommendations; comparisons to other users; evaluations of therapies on microbiome composition and functional diversity; etc.). In an example, the interface 240 can present skin-related condition information including a microbiome composition (e.g., taxonomic groups), functional diversity (e.g., relative abundance of genes associated with function correlated with skin-related conditions, as shown in FIG. 11, etc.), and/or risk of infection (e.g., of different skin-related conditions) for the user, such as relative to a user group sharing a demographic characteristic (e.g., patients sharing conditions, smokers, exercisers, users on different dietary regimens, consumers of probiotics, antibiotic users, groups undergoing particular therapies, etc.). In another example, the interface 240 can be operable to present skin-related condition information including a change in the microbiome composition over time and a change in a microbiome functional diversity over time in relation to the treatment and the skin-related condition. In a specific example, the interface's display of skin-related condition information can be improved through selection (e.g., based on components of the characterization satisfying a threshold condition, such as a skin-related condition risk exceeding a threshold, etc.) and presentation of a subset of skin-related condition information (e.g., highlighting and/or otherwise emphasizing a subset of skin-related condition information). However, the interface 240 can display any suitable information and can be configured in any suitable manner.

The system 200 and/or components of the system 200 can entirely or partially be executed by, hosted on, communicate with, and/or otherwise include: a remote computing system (e.g., a server, at least one networked computing system, stateless, stateful), a local computing system, databases (e.g., user database, microbiome dataset database, skin-related condition database, therapy database, etc.), a user device (e.g., a user smart phone, computer, laptop, supplementary medical device, wearable medical device, care provider device, etc.), and/or any suitable component. While the components of the system 200 are generally described as distinct components, they can be physically and/or logically integrated in any manner. For example, a smartphone application can partially or fully implement the microbiome characterization system 220 (e.g., apply a characterization model to generate a characterization of skin-related conditions in real-time; sequence biological samples; process microorganism sequences; extract features from microbiome datasets; etc.) and the therapy system 230 (e.g., schedule daily events at a calendar application of the smartphone to notify the user to take probiotic therapies in response to generating the characterization). However, the functionality of the system 200 can be distributed in any suitable manner amongst any suitable system components. Additionally or alternatively, the system 200 and/or method 100 can include any suitable components and/or functions analogous to (e.g., applied in the context of skin-related conditions) those described in U.S. application Ser. No. 15/452,529 filed 7 Mar. 2017, U.S. application Ser. No. 15/374,890 filed 9 Dec. 2016, U.S. application Ser. No. 14/593,424 filed 9 Jan. 2015, U.S. application Ser. No. 15/198,818 filed 30 Jun. 2016, U.S. application Ser. No. 15/098,027 filed 13 Apr. 2016, U.S. application Ser. No. 15/098,248 filed 13 Apr. 2016, U.S. application Ser. No. 15/098,236 filed 13 Apr. 2016, Ser. No. 15/098,222 filed 13 Apr. 2016, U.S. application Ser. No. 15/098,204 filed 13 Apr. 2016, U.S. application Ser. No. 15/098,174 filed 13 Apr. 2016, U.S. application Ser. No. 15/098,110 filed 13 Apr. 2016, U.S. application Ser. No. 15/098,081 filed 13 Apr. 2016, U.S. application Ser. No. 15/098,153 filed 13 Apr. 2016, U.S. application Ser. No. 15/228,890 filed 4 Aug. 2016, and U.S. application Ser. No. 15/240,919 filed 18 Aug. 2016, which are each hereby incorporated in their entirety by this reference. However, the components of the system 200 can be configured in any suitable manner.

4. Method.

Figure 1A:
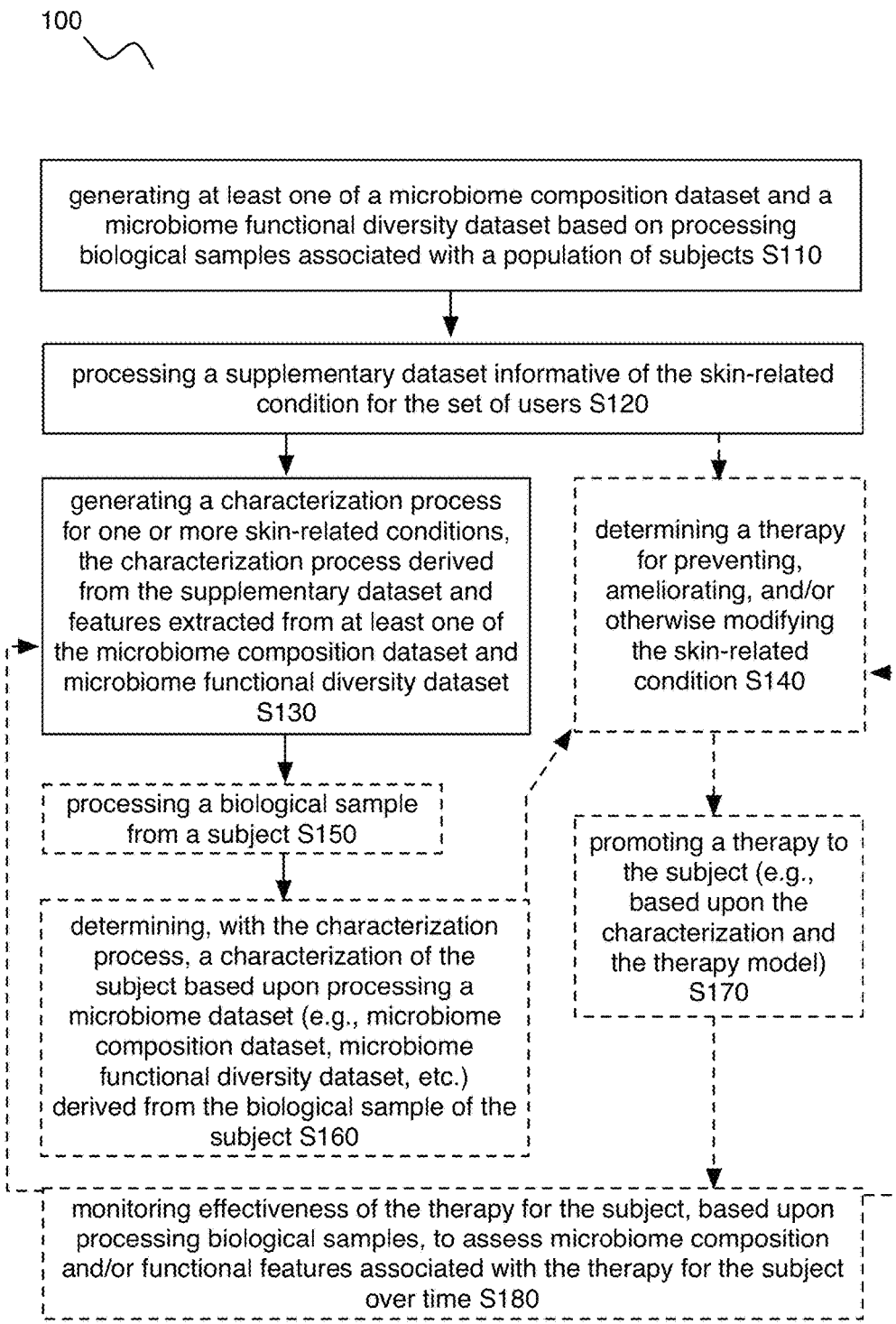
FIGS. 1A-1B are flowchart representations of variations of embodiments of a method for microbiome characterization.
Figure 1B:
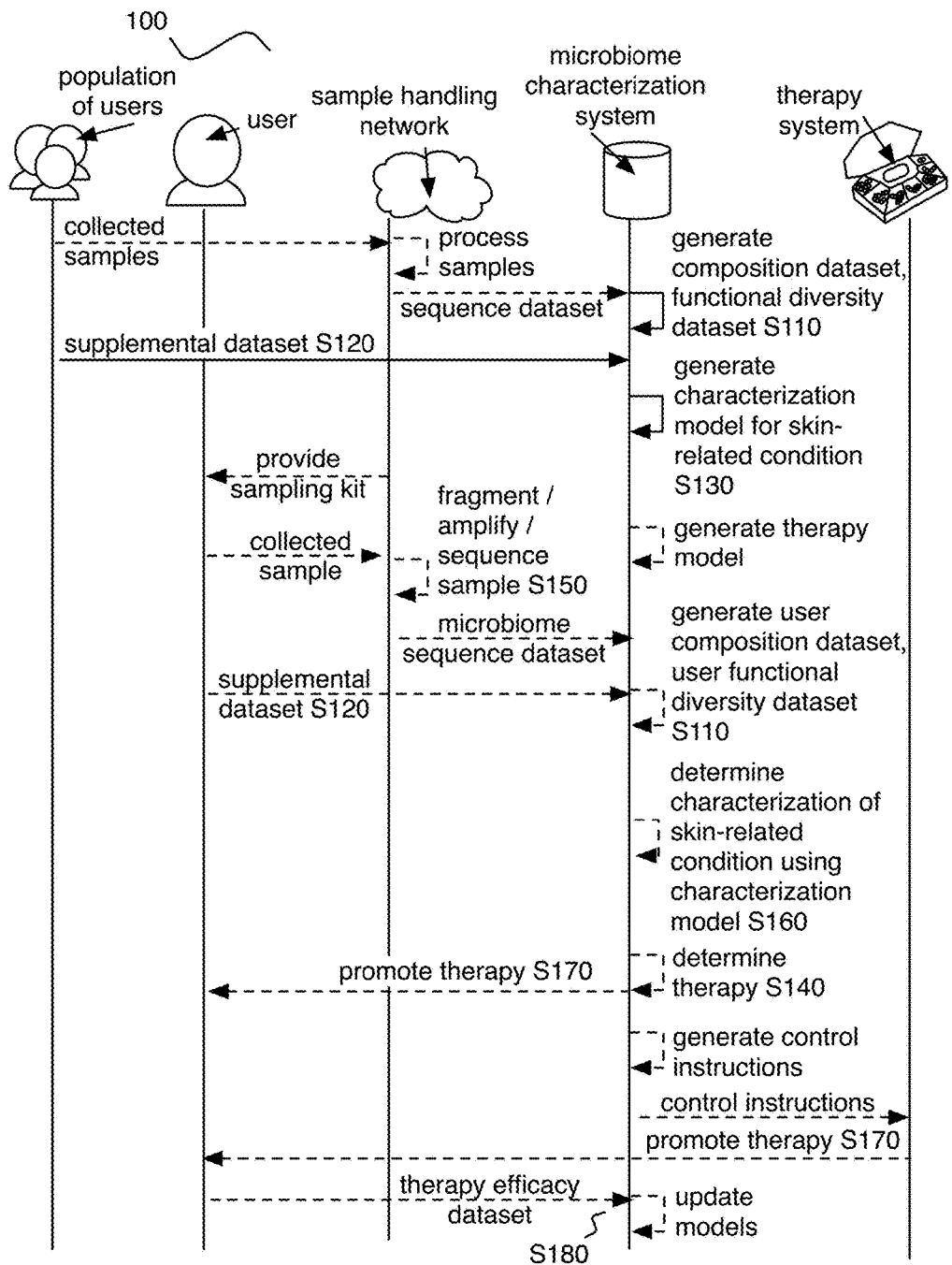

As shown in FIGS. 1A-1B and 2, embodiments of a method 100 for characterizing a skin-related condition in relation to a user can include one or more of: generating at least one of a microbiome composition dataset and a microbiome functional diversity dataset based on microorganism sequences derived from biological samples (e.g., microorganism genetic sequences derived from the samples) from a set of users S110; processing a supplementary dataset informative of the skin-related condition for the set of users S120; and performing a characterization process for one or more skin-related conditions, the characterization process derived from the supplementary dataset and features extracted from at least one of the microbiome composition dataset and microbiome functional diversity dataset S130. The method 100 can additionally or alternatively include one or more of: determining a therapy for preventing, ameliorating, and/or otherwise modifying a skin-related condition S140; processing a biological sample from a user (e.g., subject) S150; determining, with the characterization process, a characterization of the user based upon processing a microbiome dataset (e.g., microbiome composition dataset, microbiome functional diversity dataset, etc.) derived from the biological sample of the user S160; promoting a therapy for the skin-related condition to the user (e.g., based upon the characterization) S170; monitoring effectiveness of the therapy for the user, based upon processing biological samples, to assess microbiome composition and/or functional features associated with the therapy for the user over time S180; and/or any other suitable operations.

4.1 Method—Processing Datasets.

Figure 10:
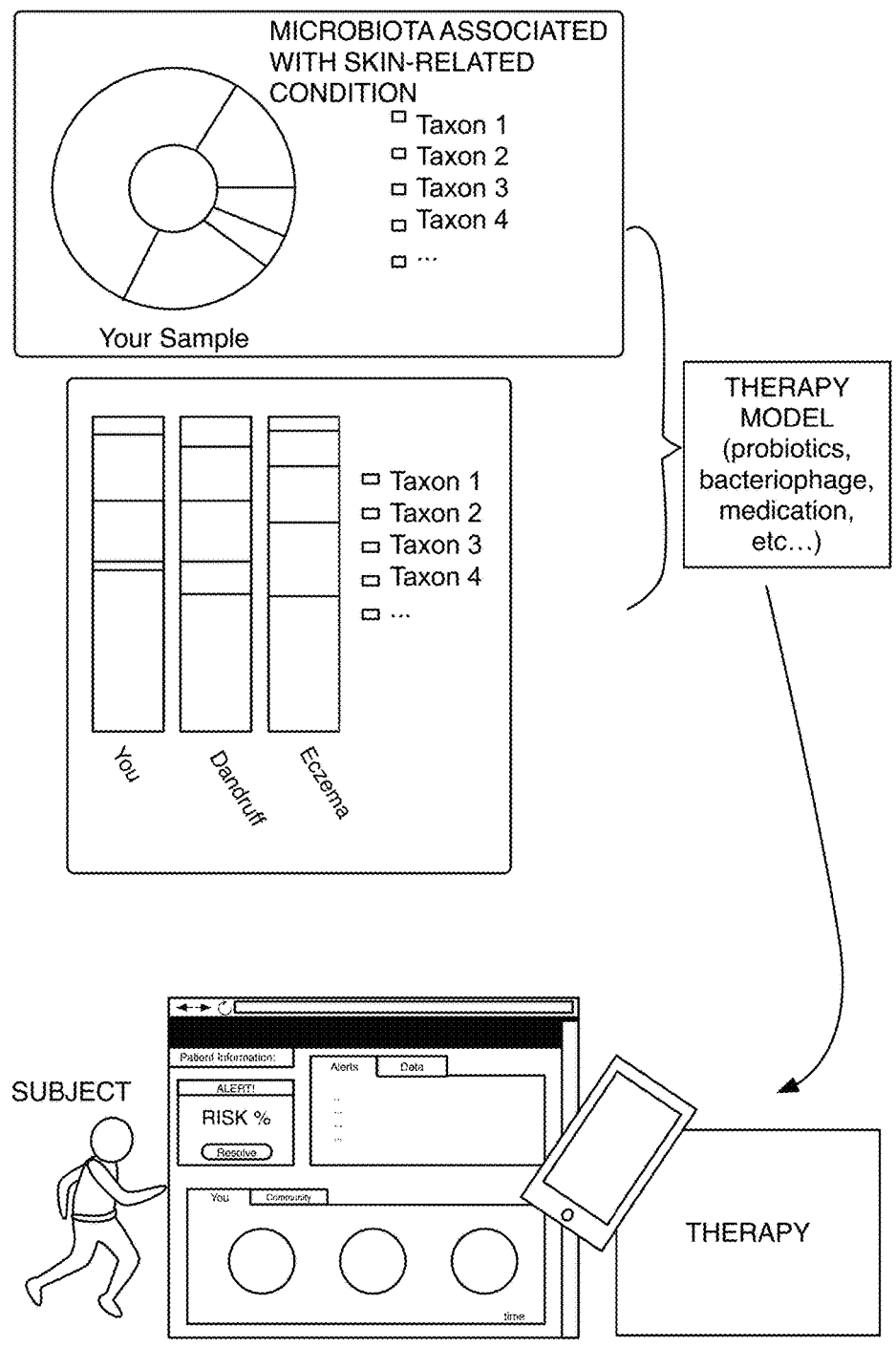
FIG. 10 depicts variations of notification provision in an embodiment of a method for microbiome characterization.

Block S110 recites: generating at least one of a microbiome composition dataset and a microbiome functional diversity dataset based on microorganism sequences derived from biological samples from a set of users. Block S110 functions to process each of an aggregate set of biological samples, in order to determine compositional and/or functional aspects associated with the microbiome of each of a population of users. As shown in FIG. 10, compositional and functional aspects can include compositional aspects at the microorganism level, including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and functional aspects can also be represented in terms of operational taxonomic units (OTUs). Compositional and functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block S110 can thus be used to provide features of interest for the characterization process of Block S130 and/or therapy process of Block S140, where the features can be microorganism-based (e.g., presence of a genus of bacteria), genetic-based (e.g., based upon representation of specific genetic regions and/or sequences) and/or functional-based (e.g., presence of a specific catalytic activity), and/or otherwise configured.

In variations of Block S110, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification (e.g., with a library preparation system) of nucleic acids from the biological sample, further purification of amplified nucleic acids of the biological sample, and sequencing of amplified nucleic acids of the biological sample, and/or any other suitable sample processing operations, such as those described in relation to U.S. application Ser. No. 15/374,890 filed 9 Dec. 2016, which is incorporated in its entirety by this reference.

In variations of Block S110 amplification of purified nucleic acids preferably includes one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Primers used in variations of Block S110 can additionally or alternatively include incorporated barcode sequences specific to each biological sample, which can facilitate identification of biological samples post-amplification. Selected primers can additionally or alternatively be associated with a skin-related condition and/or microbiome composition features (e.g., identified primers compatible with a genetic target corresponding to microbiome composition features associated with a group of taxa correlated with eczema, etc.), functional diversity features, supplementary features, and/or other features associated with the skin-related conditions. For example, the primers can be complementary to genetic targets associated with the features (e.g., genetic sequences from which relative abundance features are derived; genes associated with different skin-related conditions; etc.). Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit).

In variations of Block S110, sequencing of purified nucleic acids can include methods involving targeted amplicon sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example of Block S110, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region (e.g., 16S region, 18S region, ITS region), a reverse index sequence (e.g., corresponding to an Illumina reverse index for MiSeq/HiSeq platforms), and a reverse barcode sequence. In the specific example, sequencing includes Illumina sequencing (e.g., with a HiSeq platform, with a MiSeq platform, with a NextSeq platform, etc.) using a sequencing-by-synthesis technique.

Some variations of sample processing in Block S110 can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and any other suitable purification technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features derived from compositional and/or functional aspects of the microbiome associated with a biological sample.

In Block S110, identification of microbiome-derived sequences can include mapping of sequence data from sample processing to a subject reference genome (e.g., provided by the Genome Reference Consortium), in order to remove subject genome-derived sequences. In an example, Block S110 can include determining alignments between microorganism nucleic acid sequences and reference sequences associated with the skin-related condition (e.g., microbiome biomarkers associated with the skin-related conditions, such as biomarkers indicative of a presence and/or abundance of genetic sequences representative of groups of taxa associated with skin-related conditions; microbiome markers identified through processing microbiome datasets collected by the method 100; etc.) where generating the microbiome composition dataset and the microbiome functional diversity dataset is based on the alignments. However, mapping sequence data can be performed in any suitable manner, such as analogous to U.S. application Ser. No. 15/374,890 filed 9 Dec. 2016, which is incorporated in its entirety by this reference.

In Block S110, upon identification of represented groups of microorganisms of the microbiome associated with a biological sample, generating features derived from compositional and functional aspects of the microbiome associated with a biological sample can be performed. In one variation, generating features can include generating features based upon multilocus sequence typing (MLST), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional feature(s).

In relation to Block S110, additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (e.g., temporal changes, changes across sample sites, etc., spatial changes, etc.). However, Block S110 can be performed in any suitable manner.

Block S120 recites: receiving a supplementary dataset, associated with at least a subset of the population of users, where the supplementary dataset facilitates characterization of users. Block S120 functions to acquire additional data associated with one or more users of the set of users, which can be used to train and/or validate the characterization process generated in Block S130. In Block S120, the supplementary dataset preferably includes survey-derived data, but can additionally or alternatively include any one or more of: contextual data derived from sensors, medical data (e.g., current and historical medical data), and any other suitable type of data. In variations of Block S120 including reception of survey-derived data, the survey-derived data preferably provides physiological, demographic, and behavioral information in association with a user. However, types of supplementary data and manners of collecting supplementary data can be analogous to that described in U.S. application Ser. No. 15/374,890 filed 9 Dec. 2016, which is incorporated in its entirety by this reference, but processing supplementary datasets can be performed in any suitable manner.

4.2 Method—Performing a Characterization Process.

Block S130 recites: performing a characterization process for one or more skin-related conditions, the characterization process derived from the supplementary dataset and features extracted from at least one of the microbiome composition dataset and microbiome functional diversity dataset S130. Block S130 functions to identify features and/or feature combinations that can be used to characterize users or groups based upon their microbiome composition and/or functional features. As such, the characterization process can be used as a diagnostic tool that can characterize a user (e.g., in terms of behavioral traits, in terms of medical conditions, in terms of demographic traits, etc.) based upon their microbiome composition and/or functional features, in relation to one or more of their health condition states, behavioral traits, medical conditions, demographic traits, and any other suitable traits. Such characterization can then be used to suggest or provide personalized therapies by way of the therapy model of Block S140.

In performing the characterization process, Block S130 can use computational methods (e.g., statistical methods, machine learning methods, artificial intelligence methods, bioinformatics methods, etc.) to characterize a user as exhibiting features characteristic of a group of users with a health condition. However, the characterization process can be performed in any suitable manner.

In variations of Block S130, performing a characterization process can include generating one or more characterizations of one or more skin-related conditions. In some examples, the characterization process of Block S130 can facilitate identification of which microorganism population(s) (e.g., taxonomic groups, microbiome composition features, etc.) are upregulated or downregulated in relation to skin-related conditions, and/or which microbiome functional aspects (e.g., in relation to Clusters of Orthologous Groups/Kyoto Encyclopedia of Genes and Genomes pathways, microbiome functional diversity features, etc.) are upregulated or downregulated in relation to skin-related conditions. Characterizing upregulation and/or downregulation can be at any suitable taxonomic level (e.g., kingdom, phylum, class, order, family, genus, species, strain, etc.), any suitable granularity of functional diversity, and/or at any suitable granularity.

In another variation, characterizing a skin-related condition in Block S130 can include generating a diagnostic analysis (e.g., estimating a risk of being inflicted by the skin-related condition; calculating the change in risk conferred by an identified therapy; diagnosing the presence of the skin-related condition; diagnosing the severity of the skin-related condition over time in relation to microbiome composition and/or functional diversity; etc.) and/or associated complications. In another variation of Block S130, characterizing a skin-related condition can be based on one or more supplementary datasets. For example, the set of feature-selection rules can correlate one or more skin-related conditions to one or more biometric features derived from biometric sensor data informative of a skin-related condition (e.g., optical data of the skin such as skin lesions, acne, etc.; skin-related parameters, such as cutaneous hydration, associated with skin-related conditions; blood data; temperature data; user behavior data; temperature data; cardiovascular data; stool data; etc.). In another example, performing a characterization process can include determining a series of characterizations over time based on therapies promoted over time (e.g., based on therapy data including antibiotic regimen data, probiotic regimen data, and/or other suitable therapy data collected over time and associated with a population of users), where the effect of different therapies over time can aid in illuminating insights associated with microbiome compositions and/or functional diversity correlated with skin-related conditions. However, performing a characterization process in relation to a skin-related condition can be performed in any suitable manner.

Block S130 can additionally or alternatively include Block S132: generating features, which can function to generate one or more features for the characterization process (e.g., for use in training a characterization model). Features can include any one or more of: microbiome composition features (e.g., absolute and/or relative abundance of taxonomic groups in a user's microbiome), microbiome functional diversity features, and/or other suitable features. Microbiome functional diversity features can include any one or more of: Kyoto Encyclopedia of Genes and Genomes (KEGG) functional features (e.g., KEGG features associated with flagellum biosynthesis, etc.), Clusters of Orthologous Groups (COG) of proteins features, L2, L3, L4 derived features, genomic functional features, functional features associated with and/or specific to a taxonomic group, chemical functional features (e.g., cysteine metabolism, etc.), systemic functional features (e.g., systemic immune function; functions associated with systemic diseases; etc.), and/or any suitable functional features. Microbiome features can additionally or alternatively be derived from and/or associated with at least one of: relative abundance monotonic transformations, non-monotonic transformations, normalizations, feature vectors such as derived from at least one of linear latent variable analysis and nonlinear latent variable analysis, linear regression, nonlinear regression, kernel methods, feature embedding methods, machine learning, statistical inference methods and/or any other suitable approaches.

Regarding Block S132, determining features is preferably based on processing microbiome composition data and/or microbiome functional diversity data according to one or more computer-implemented rules (e.g., a feature-selection rule, a user preference rule, etc.), but features can be determined based on any suitable information. For example, the method 100 can include obtaining a set of skin-related feature-selection rules correlating the skin-related condition to a subset of microbiome composition features and/or a subset of microbiome functional diversity features (e.g., from a pool of potential microbiome composition and/or functional diversity features); and generating features based on evaluating the microbiome composition data and the microbiome functional diversity data against the set of skin-related feature-selection rules, where the set of skin-related feature selection rules are operable to improve the microbiome characterization system (e.g., by facilitating decreased processing time such as for transforming supplementary data and features into a characterization model; by improving speed of model retrieval, and/or execution; by improving characterization and/or therapy provision accuracy; etc.). Block S132 and/or other portions of the method 100 preferably include applying computer-implemented rules to process population-level data, but can additionally or alternatively include applying computer-implemented rules to process microbiome-related data on a demographic-specific basis (e.g., subgroups sharing a demographic feature such as skin hygiene regimens, ethnicity, age, gender, etc.), condition-specific basis (e.g., subgroups exhibiting a particular skin-related condition), a sample type-specific basis (e.g., applying different computer-implemented rules to process microbiome data derived from skin samples versus fecal matter samples), and/or any other suitable basis. As such, Block S132 can include assigning users from the population of users to one or more subgroups; and applying different computer-implemented rules for determining features (e.g., the set of feature types used; the types of characterization models generated from the features; etc.) for the different subgroups.

Figure 12:
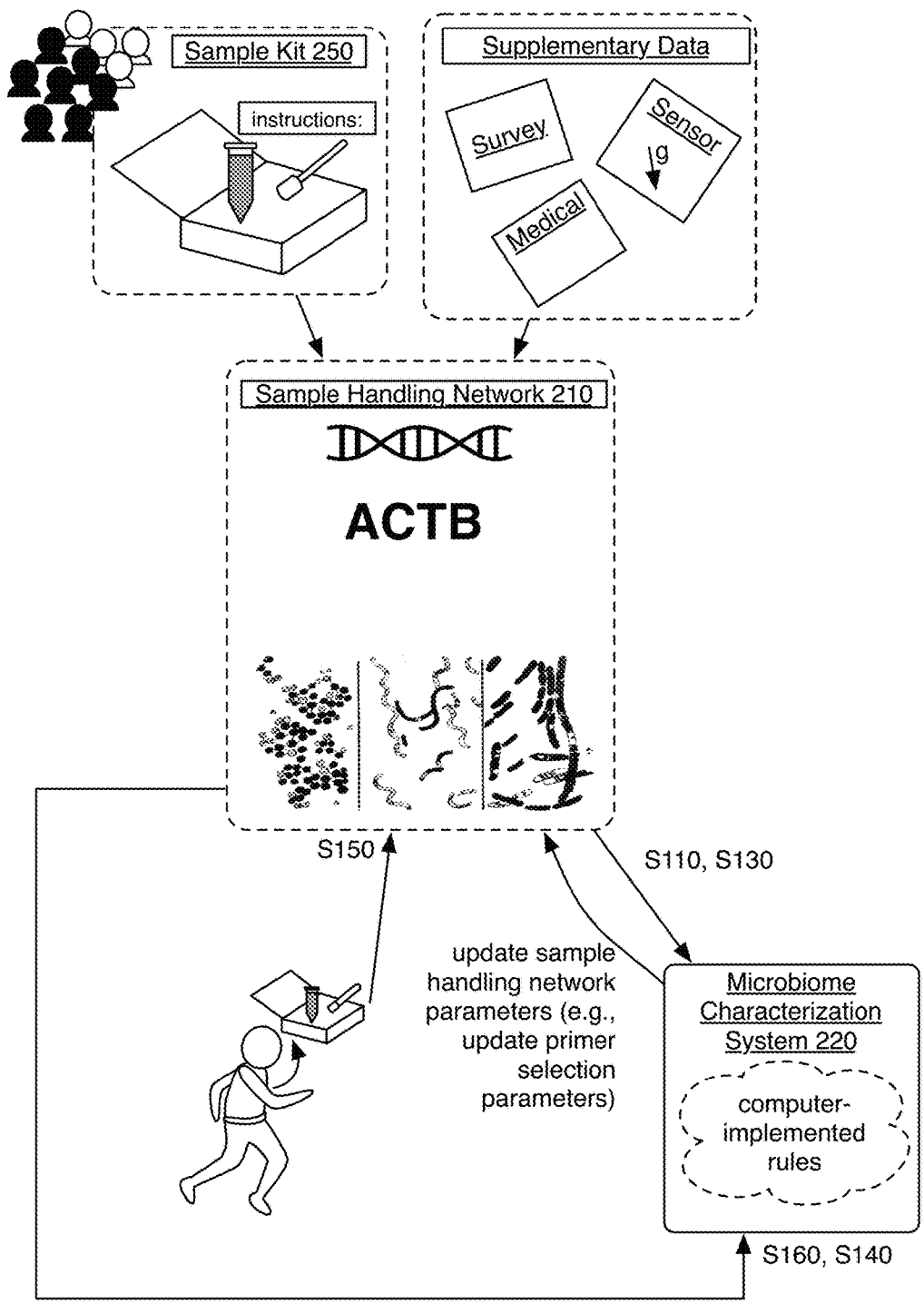
FIG. 12 depicts a variation of sample processing parameter modification in an embodiment of a method for microbiome characterization.

In a variation, Block S132 can include applying feature-selection rules (e.g., feature selection algorithms such as exhaustive, best first, simulated annealing, greedy forward, greedy backward, and/or other suitable feature selection algorithms) to filter, rank, and/or otherwise select features for use in generating one or more characterization models (e.g., using skin-related feature-selection rules correlating one or more skin-related conditions to microbiome composition features and/or microbiome functional diversity features, etc.), therapy models (e.g., using rules correlating one or more therapies to one or more microbiome composition features, microbiome functional diversity features, and/or features derived from characterizations generated in Block S160, etc.), and/or other suitable models. As shown in FIG. 12, in a variation, application of feature-selection rules can lead to microbiome-related insights upon which modifications in sample processing (e.g., parameters such as techniques, experimental conditions, in Blocks S110-S120, S150, etc.) can be based. For example, the method 100 can include: applying a set of skin-related feature selection rules to identify features (e.g., microbiome composition features indicating particular taxonomic groups; microbiome functional diversity features indicating particular microorganism functions) correlated (e.g., most correlated; etc.) with the skin-related conditions (e.g., presence, risk, therapies, etc.); and selecting primers (e.g., for use in amplification and sequencing to generate microbiome datasets; etc.) compatible with genetic targets associated with the identified features (e.g., using primers associated with genetic targets corresponding to the microbiome functional diversity features correlated with the skin-related condition; etc.). As such, the feature-selection rules and/or other computer-implemented rules can additionally or alternatively function to determine sample processing parameters (e.g., described in relation to Blocks S110-S120, S150, etc.). Additionally or alternatively, applying feature-selection rules can be performed in a manner analogous to U.S. application Ser. No. 15/452,529 filed 7 Mar. 2017, which is herein incorporated in its entirety by this reference, and/or can be performed in any suitable manner. However, any suitable number and/or type of feature-selection rules can be applied in any manner to define one or more feature sets.

In an example, in Block S132, feature-selection rules can include application of a statistical analysis (e.g., an analysis of probability distributions) of similarities and/or differences between a first group of users exhibiting a target state (e.g., a health condition state) and a second group of users not exhibiting the target state (e.g., a "normal" state). In implementing this variation, one or more of a Kolmogorov-Smirnov (KS) test, a permutation test, a Cramér-von Mises test, and any other statistical test (e.g., t-test, z-test, chi-squared test, test associated with distributions, etc.) can be used. In particular, one or more such statistical hypothesis tests can be used to assess a set of features having varying degrees of abundance in a first group of users exhibiting a target state (e.g., a sick state) and a second group of users not exhibiting the target state (e.g., having a normal state). In more detail, the set of features assessed can be constrained based upon percent abundance and/or any other suitable parameter pertaining to diversity in association with the first group of users and the second group of users, in order to increase or decrease confidence in the characterization. In a specific implementation of this example, a feature can be derived from a taxon of bacteria that is abundant in a certain percentage of users of the first group and users of the second group, where a relative abundance of the taxon between the first group of users and the second group of users can be determined from the KS test, with an indication of significance (e.g., in terms of p-value). Thus, an output of Block S132 can include a normalized relative abundance value (e.g., 25% greater abundance of a taxon in sick users vs. healthy users) with an indication of significance (e.g., a p-value of 0.0013). Variations of feature generation can additionally or alternatively implement or be derived from functional features or metadata features (e.g., non-bacterial markers)

In another variation, Block S132 can additionally or alternatively transform input data from at least one of the microbiome composition diversity dataset and microbiome functional diversity dataset into feature vectors that can be tested for efficacy in predicting characterizations of the population of users. Data from the supplementary dataset can be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of user features, of combinations of features) having high correlation with specific classifications of users.

In variations of Block S132, feature vectors effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and/or any other suitable features derived from the microbiome diversity dataset and/or the supplementary dataset. For example, Block S132 can include generating a set of microbiome feature vectors (e.g., a feature vector for each user of subgroup or population of users) based on microbiome composition features (e.g., a subset selected based on feature-selection rules), microbiome functional diversity features (e.g., a subset selected based on feature-selection rules), and supplementary features (e.g., biometric features derived from the supplementary biometric sensor data, etc.), where the set of microbiome feature vectors can be used in training the characterizations model and/or other suitable models. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors and features can additionally or alternatively be determined in any other suitable manner.

Block S130 can additionally or alternatively include Block S134: generating a characterization model. Block S134 functions to generate one or more characterization models for skin-related conditions based on applying one or more features, microbiome datasets, supplementary data, and/or any other suitable data. Characterization models (and/or therapy models or other suitable models) can include any one or more of: probabilistic properties, heuristic properties, deterministic properties, and/or any other suitable properties. Block S134 and/or any other suitable portions of the method 100 (e.g., generating a therapy model S140) can employ one or more algorithms analogous to those described in U.S. application Ser. No. 15/452,529 filed 7 Mar. 2017 and/or U.S. application Ser. No. 15/374,890 filed 9 Dec. 2016, which are incorporated in their entirety by this reference, but any suitable algorithms can be employed.

In an example of Block S134, a characterization model can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model. In another example, characterization of the user(s) can additionally or alternatively implement use of a high false positive test and/or a high false negative test to further analyze sensitivity of the characterization process in supporting analyses generated according to embodiments of the method 100. However, preventing bias and/or improving sensitivity can be performed in any suitable manner.

Figure 5:
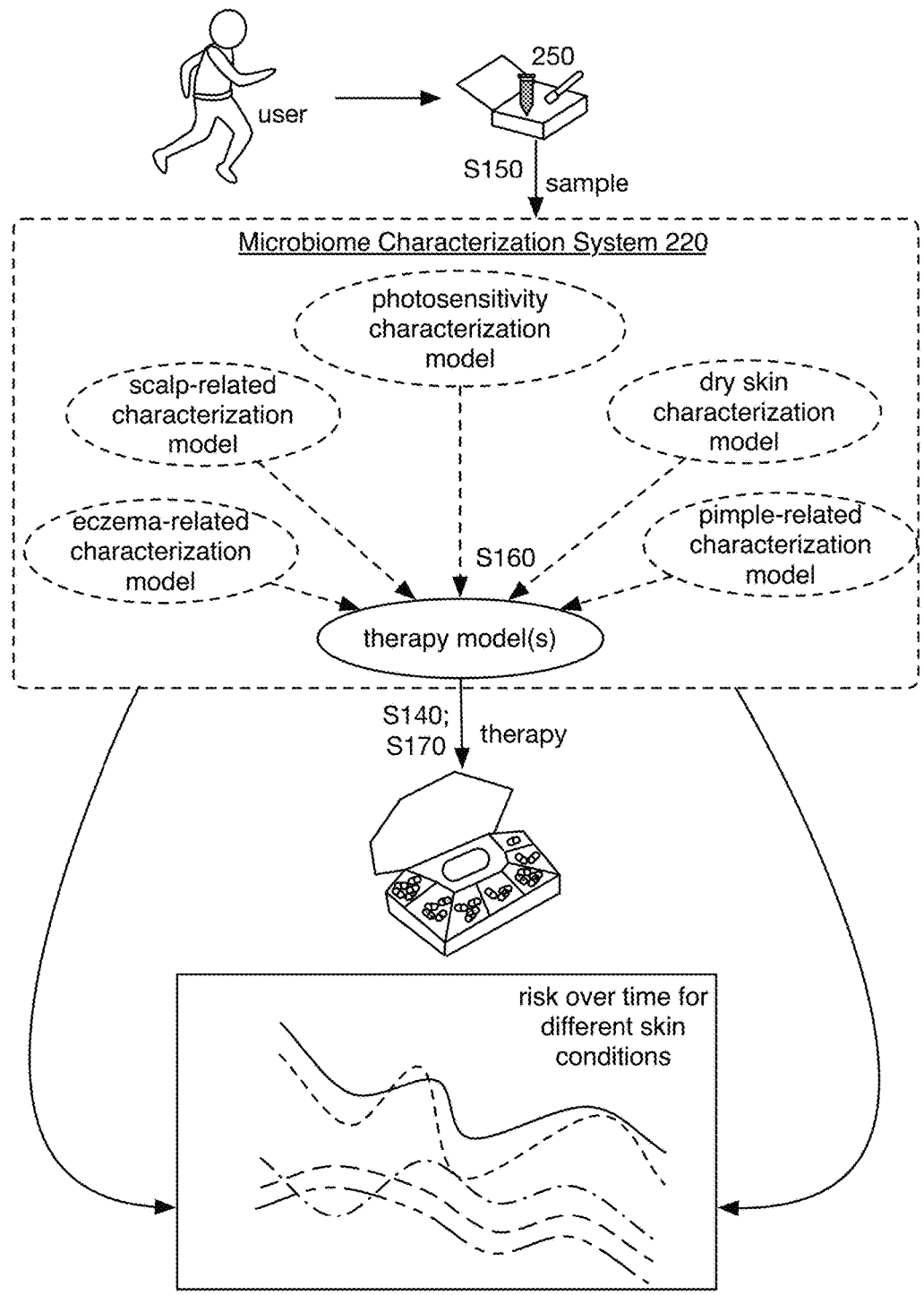
FIG. 5 depicts a variation of applying multiple characterization models in an embodiment of a method for microbiome characterization.

In another variation of Block S134, different characterization models can be generated for different demographic groups (e.g., a first characterization model characterizing a skin-related condition for users who bathe on a daily basis, a second characterization model for users who bathe on a non-daily basis, etc.), skin-associated conditions (e.g., different characterization models for eczema, dry skin, pimple-related conditions, scalp-related conditions, photosensitivity, dandruff, etc., as shown in FIG. 5), individual users, supplementary data (e.g., models incorporating features derived from biometric sensor data and/or survey response data vs. models independent of supplementary data, etc.), and/or other suitable criteria. In an example, the method 100 can include generating a first characterization model (e.g., eczema-related characterization model for eczema) based on a first feature set derived from at least one of the microbiome composition dataset and microbiome functional diversity dataset; and generating one or more additional characterization models (e.g., scalp-related characterization model for scalp-related conditions; dry-skin related characterization model for dry skin-related conditions; etc.) based on additional feature sets (e.g., sharing feature types with the first feature set or other feature sets; including a set of feature types distinct from those of the first feature set or other feature sets; etc.) derived from the at least one of the microbiome composition dataset and the microbiome functional diversity dataset, and/or other suitable data (e.g., other microbiome composition datasets and/or functional diversity datasets, etc.). As shown in FIG. 5, characterizations outputted from different characterization models can be used in determining and/or promoting a therapy, such as by inputting features derived from a different characterizations (e.g., outputs by an eczema-related characterization model, a scalp-related characterization model, dry skin-related characterization model, etc.) into a therapy model (e.g., to generate a single therapy or a plurality of therapies tailored to treating the different skin-related conditions, etc.).

In another example, Block S134 can include generating a characterization model for a demographic group of users sharing a skin hygiene characteristic (e.g., using moisturizer, bathing, sunscreen, at a particular frequency, etc.); associating the characterization model with user accounts (e.g., at a database of the microbiome characterization system) for the users who indicate the skin hygiene characteristic (e.g., at a digital survey presented by the interface; based on user device sensor data such as location data); and retrieving the characterization model (e.g., from the database) for characterizing the users. Generating a plurality of characterization models suited to different contexts can confer improvements to the microbiome characterization system by improving characterization accuracy (e.g., by tailoring analysis to a particular user's demographic and/or situation, etc.), retrieval speed for the appropriate characterization model from a database (e.g., by associating customized characterization models with particular user accounts and/or other identifiers), training and/or execution of characterization models (e.g., where the customized models are associated with a subset of a pool of potential features correlated with skin-related conditions, and where the remaining unselected features are less correlated with the skin-related conditions), and/or other suitable aspects of the microbiome characterization system.

In another variation of Block S134, generating feature sets for different characterization models (and/or therapy models) can be based on different feature selection rules (e.g., applying eczema-associated feature-selection rules to generate a feature set specific to eczema in generating an eczema-related characterization model, etc.). Alternatively, overlapping or the same set of feature selection rules can be used for generating different characterization models (e.g., using the same functional diversity feature in generating two different characterization models for two different skin-related conditions, etc.). Additionally or alternatively, generating any number of characterization models can be performed in any suitable manner.

In another variation of Block S134, performing a characterization process can be based upon statistical analyses that identify the sets of features that have the highest correlations with one or more skin-related conditions for which one or more therapies would have a positive effect, based upon a Kolmogorov-Smirnov statistical test that compares a dataset derived from a subset of the population of users that present the skin-related condition, and a dataset derived from a subset of the population of users that do not present the skin-related condition. However, performing characterization processes can be performed in any suitable manner.

4.2.1 Characterization Process—Photosensitivity Characterization

In variations of Block S130, performing a characterization process can be for one or more photosensitivity-associated conditions. In particular, photosensitivity can be a skin condition characterized by an abnormal reaction of the skin to a component of the electromagnetic spectrum of sunlight. It is typically diagnosed by skin examination, phototests and photopatch tests. In addition, photosensitivity-associated conditions can be associated with specific microbiota diversity and/or health conditions related to relative abundance of gut microorganisms, and/or microbiome functional diversity.

In variations of Block S130, a set of features useful for characterizations of photosensitivity-associated conditions and/or other skin-associated conditions can include features derived from one or more of the following taxa: *Marvinbryantia* (genus), Erysipelotrichales (order), Erysipelotrichia (class), Bacteroidetes (phylum), and/or any other suitable taxa. Thus, characterization of the subject comprises characterization of the subject as someone with photosensitivity based upon detection of one or more of the above features, in a manner that is an alternative or supplemental to typical methods of diagnosis. In variations of the specific example, the set of features can, however, include any other suitable features useful for diagnostics.

Additionally or alternatively, in Block S130, the set of features can include functional features (e.g., diversity features) associated with photosensitivity-associated conditions (e.g., associated with photosensitivity diagnostics using skin samples) and/or other skin-associated conditions, including one or more of: COG derived features, KEGG L2, L3, L4 derived features, and any other suitable functional features. In specific examples, such features can include: an infectious diseases KEGG L2 derived feature.

However, performing the characterization process for photosensitivity-associated conditions can be performed in any suitable manner using any suitable features.

4.2.2 Characterization Process—Dry Skin Characterization.

In variations of Block S130, performing a characterization process can be for one or more dry skin-associated conditions. In particular, dry skin can be characterized by rough skin, itching, flaking, scaling or peeling, fine lines or cracks, gray skin in people with dark skin, redness, deep cracks that may bleed and which can lead to infections. In addition, dry skin-associated conditions can be associated with specific microbiota diversity and/or health conditions related to relative abundance of gut microorganisms, and/or microbiome functional diversity.

In variations of the characterization process of Block S130, a set of features useful for characterizations of dry skin-associated conditions and/or other skin-associated conditions can include features derived from one or more of the following taxa: *Staphylococcus* (genus), Staphylococcaceae (family), Bacillales (order), Actinobacteria (class), Firmicutes (phylum), Actinobacteria (phylum), *Propionibacterium* (genus), and/or any other suitable taxa, where sampling of subjects can involve sampling of the skin and/or other body region. Thus, characterization of the subject comprises characterization of the subject as someone with dry skin based upon detection of one or more of the above features, in a manner that is an alternative or supplemental to typical methods of diagnosis. In variations of the specific example, the set of features can, however, include any other suitable features useful for diagnostics.

Additionally or alternatively, in Block S130, the set of features can include functional diversity features associated with dry skin-associated conditions (e.g., associated with dry skin diagnostics using skin samples) and/or other skin-associated conditions, including one or more of: COG derived features, KEGG L2, L3, L4 derived features and/or any other suitable combination of features. However, performing the characterization process for dry skin-associated conditions can be performed in any suitable manner using any suitable features.

4.2.3 Characterization Process—Dandruff Characterization

In variations of Block S130, performing a characterization process can be for one or more scalp-related conditions. In particular, dandruff can be a chronic scalp condition characterized by flaking, itching and scaling of the skin in the scalp, that can be caused by dry skin, irritated oily skin, sensitivity to hair care products, that finally results in an imbalance of the scalp microbiome. In addition, scalp-related conditions can be associated with specific microbiota diversity and/or health conditions related to relative abundance of gut microorganisms, and/or microbiome functional diversity.

In variations of Block S130, a set of features useful for characterizations of dandruff conditions and/or other scalp-associated conditions can include features derived from one or more of the following taxa: Propionibacterium sp. MSP09A (species), Bacteroides vulgatus (species, Streptococcus sp. BS35a (species), Staphylococcus sp. C912 (species), Phascolarctobacterium sp. 377 (species), Faecalibacterium prausnitzii (species), Alistipes putredinis (species), Alistipes sp. EBA6-25cl2 (species), Alistipes sp. RMA 9912 (species) Anaerostipes sp. 5_1_63FA (species), Bacteroides acidifaciens (species), Bacteroides caccae (species), Bacteroides fragilis (species), Bacteroides plebeius (species), Bacteroides sp. AR20 (species), Bacteroides sp. AR29 (species), Bacteroides sp. D22 (species), Bacteroides sp. DJF (species), Bacteroides sp. SLC1-38 (species), Bacteroides sp. XB12B (species), Bacteroides vulgatus (species), Blautia faecis (species), Blautia luti (species), Blautia sp. YHC-4 (species), Blautia stercoris (species), Blautia wexlerae (species), Collinsella aerofaciens (species), Corynebacterium sp. (species), Corynebacterium spheniscorum (species), Corynebacterium ulcerans (species), Dorea formicigenerans (species), Dorea longicatena (species), Lachnospira pectinoschiza (species), Odoribacter splanchnicus (species), Parabacteroides distasonis (species), Parabacteroides merdae (species), Phascolarctobacterium faecium (species), Propionibacterium acnes (species), Propionibacterium granulosum (species), Propionibacterium sp. MSP09A (species), Roseburia intestinalis (species), Roseburia inulinivorans (species), Roseburia sp. 11SE39 (species), Staphylococcus sp. C912 (species), Staphylococcus sp. WB18-16 (species), Streptococcus sp. BS35a (species), Streptococcus sp. oral taxon G59 (species), Streptococcus thermophilus (species), Subdoligranulum variabile (species), Sutterella stercoricanis (species), Sutterella wadsworthensis Propionibacterium (genus), Staphylococcus (genus), Roseburia (genus), Blautia (genus), Bacteroides (genus), Pseudobutyrivibrio (genus), Alistipes (genus), Faecalibacterium (genus), Collinsella (genus), Clostridium (genus), Anaerostipes (genus), Dorea (genus), Subdoligranulum (genus), Sarcina (genus), Lachnospira (genus), Anaerotruncus (genus), Parabacteroides (genus), Flavonifractor (genus), Intestinibacter (genus), Erysipelatoclostridium (genus), Phascolarctobacterium (genus), Streptococcus (genus), Odoribacter (genus), Sutterella (genus), Bifidobacterium (genus), Corynebacterium (genus), Bilophila (genus), Terrisporobacter (genus), Dialister (genus), Prevotella (genus), Marvinbryantia (genus), Propionibacteriaceae (family), Staphylococcaceae (family), Porphyromonadaceae (family), Lachnospiraceae (family), Peptostreptococcaceae (family), Coriobacteriaceae (family), Clostridiaceae (family), Ruminococcaceae (family), Bacteroidaceae (family), Erysipelotrichaceae (family), Rikenellaceae (family), Prevotellaceae (family), Sutterellaceae (family), Flavobacteriaceae (family), Streptococcaceae (family), Veillonellaceae (family), Acidaminococcaceae (family), Desulfovibrionaceae (family), Oscillospiraceae (family), Bifidobacteriaceae (family), Corynebacteriaceae (family), Pasteurellaceae (family), Bacteroidales (order), Actinomycetales (order), Selenomonadales (order), Bacillales (order), Coriobacteriales (order), Clostridiales (order), Erysipelotrichales (order), Lactobacillales (order), Burkholderiales (order), Flavobacteriales (order), Desulfovibrionales (order), Bifidobacteriales (order), Pasteurellales (order), Actinobacteria (class), Bacteroidia (class), Negativicutes (class), Betaproteobacteria (class), Clostridia (class), Erysipelotrichia (class), Flavobacteriia (class), Bacilli (class), Deltaproteobacteria (class), Gammaproteobacteria (class), Bacteroidetes (phylum), Actinobacteria (phylum), Proteobacteria (phylum), Firmicutes (phylum), Verrucomicrobia (phylum), and/or any other suitable taxa. Thus, characterization of the subject comprises characterization of the subject as someone with dandruff based upon detection of one or more of the above features, in a manner that is an alternative or supplemental to typical methods of diagnosis. In variations of the specific example, the set of features can, however, include any other suitable features useful for diagnostics.

Additionally or alternatively, in Block S130, the set of features can include functional diversity features associated with scalp-related conditions (e.g., associated with dandruff diagnostics using skin samples) and/or other skin-associated conditions, including one or more of: COG derived features, KEGG L2, L3, L4 derived features, and any other suitable functional diversity features. In specific examples, such features can include one or more of: a glycan biosynthesis and metabolism KEGG L2 derived feature, an environmental adaptation KEGG L2 derived feature, a cancers KEGG L2 derived feature, an immune system diseases KEGG L2 derived feature, a transcription KEGG L2 derived feature, a signaling molecules and interaction KEGG L2 derived feature, a membrane transport KEGG L2 derived feature, a cell motility KEGG L2 derived feature, a cellular processes and signaling KEGG L2 derived feature, a metabolism of cofactors and vitamins KEGG L2 derived feature, a metabolism KEGG L2 derived feature, a neurodegenerative diseases KEGG L2 derived feature, a metabolic diseases KEGG L2 derived feature, an enzyme families KEGG L2 derived feature, a cell growth and death KEGG L2 derived feature, a carbohydrate metabolism KEGG L2 derived feature, a transport and catabolism KEGG L2 derived feature, a genetic information processing KEGG L2 derived feature, a replication and repair KEGG L2 derived feature, an energy metabolism KEGG L2 derived feature, a digestive system KEGG L2 derived feature, an amino acid metabolism KEGG L2 derived feature, a metabolism of other amino acids KEGG L2 derived feature, a biosynthesis of other secondary metabolites KEGG L2 derived feature, a folding, sorting and degradation KEGG L2 derived feature, a lipid metabolism KEGG L2 derived feature, an infectious diseases KEGG L2 derived feature, a nucleotide metabolism KEGG L2 derived feature, a metabolism of terpenoids and polyketides KEGG L2 derived feature, a renal cell carcinoma KEGG L3 derived feature, an ubiquinone and other terpenoid-quinone biosynthesis KEGG L3 derived feature, an amyotrophic lateral sclerosis KEGG L3 derived feature, a lipoic acid metabolism KEGG L3 derived feature, a cyanoamino acid metabolism KEGG L3 derived feature, a glutathione metabolism KEGG L3 derived feature, a toluene degradation KEGG L3 derived feature, a riboflavin metabolism KEGG L3 derived feature, a plant-pathogen interaction KEGG L3 derived feature, a prenyltransferases KEGG L3 derived feature, a biosynthesis of ansamycins KEGG L3 derived feature, an ABC transporters KEGG L3 derived feature, an inositol phosphate metabolism KEGG L3 derived feature, a citrate cycle (TCA cycle) KEGG L3 derived feature, a chromosome KEGG L3 derived feature, a glycolysis/gluconeogenesis KEGG L3 derived feature, a valine, leucine and isoleucine degradation KEGG L3 derived feature, a primary immunodeficiency KEGG L3 derived feature, a DNA replication proteins KEGG L3 derived feature, a cytoskeleton proteins KEGG L3 derived feature, a peroxisome KEGG L3 derived feature, a transcription machinery KEGG L3 derived feature, a protein folding and associated processing KEGG L3 derived feature, a d-alanine metabolism KEGG L3 derived feature, a translation proteins KEGG L3 derived feature, a glycine, serine and threonine metabolism KEGG L3 derived feature, a lipopolysaccharide biosynthesis proteins KEGG L3 derived feature, an energy metabolism KEGG L3 derived feature, a lipid metabolism KEGG L3 derived feature, a peptidases KEGG L3 derived feature, a carbohydrate digestion and absorption KEGG L3 derived feature, a caprolactam degradation KEGG L3 derived feature, a glycerolipid metabolism KEGG L3 derived feature, a carbon fixation in photosynthetic organisms KEGG L3 derived feature, a membrane and intracellular structural molecules KEGG L3 derived feature, a fatty acid biosynthesis KEGG L3 derived feature, a type I diabetes mellitus KEGG L3 derived feature, a phosphotransferase system (pts) KEGG L3 derived feature, a base excision repair KEGG L3 derived feature, a sporulation KEGG L3 derived feature, a transporters KEGG L3 derived feature, a protein kinases KEGG L3 derived feature, a pantothenate and CoA biosynthesis KEGG L3 derived feature, a cell cycle—Caulobacter KEGG L3 derived feature, a butirosin and neomycin biosynthesis KEGG L3 derived feature, a mismatch repair KEGG L3 derived feature, a pores ion channels KEGG L3 derived feature, an oxidative phosphorylation KEGG L3 derived feature, a cell division KEGG L3 derived feature, a replication, recombination and repair proteins KEGG L3 derived feature, a bacterial motility proteins KEGG L3 derived feature, a carbon fixation pathways in prokaryotes KEGG L3 derived feature, a transcription factors KEGG L3 derived feature, a vitamin b6 metabolism KEGG L3 derived feature, a chloroalkane and chloroalkene degradation KEGG L3 derived feature, a peptidoglycan biosynthesis KEGG L3 derived feature, a drug metabolism—other enzymes KEGG L3 derived feature, a proteasome KEGG L3 derived feature, a RNA transport KEGG L3 derived feature, an ascorbate and aldarate metabolism KEGG L3 derived feature, a cysteine and methionine metabolism KEGG L3 derived feature, a galactose metabolism KEGG L3 derived feature, a tetracycline biosynthesis KEGG L3 derived feature, a translation factors KEGG L3 derived feature, a glycerophospholipid metabolism KEGG L3 derived feature, a pentose phosphate pathway KEGG L3 derived feature, a tyrosine metabolism KEGG L3 derived feature, a photosynthesis proteins KEGG L3 derived feature, a *Vibrio cholerae* pathogenic cycle KEGG L3 derived feature, an amino sugar and nucleotide sugar metabolism KEGG L3 derived feature, a bacterial chemotaxis KEGG L3 derived feature, a tryptophan metabolism KEGG L3 derived feature, a nicotinate and nicotinamide metabolism KEGG L3 derived feature, a histidine metabolism KEGG L3 derived feature, a biotin metabolism KEGG L3 derived feature, a secretion system KEGG L3 derived feature, a cellular antigens KEGG L3 derived feature, a sulfur relay system KEGG L3 derived feature, a taurine and hypotaurine metabolism KEGG L3 derived feature, a photosynthesis KEGG L3 derived feature, a zeatin biosynthesis KEGG L3 derived feature, a methane metabolism KEGG L3 derived feature, a RNA degradation KEGG L3 derived feature, a phosphatidylinositol signaling system KEGG L3 derived feature, a glyoxylate and dicarboxylate metabolism KEGG L3 derived feature, an adipocytokine signaling pathway KEGG L3 derived feature, a starch and sucrose metabolism KEGG L3 derived feature, a chaperones and folding catalysts KEGG L3 derived feature, a vitamin metabolism KEGG L3 derived feature, a pyruvate metabolism KEGG L3 derived feature, a porphyrin and chlorophyll metabolism KEGG L3 derived feature, a geraniol degradation KEGG L3 derived feature, a tuberculosis KEGG L3 derived feature, a tropane, piperidine and pyridine alkaloid biosynthesis KEGG L3 derived feature, a beta-alanine metabolism KEGG L3 derived feature, a PPAR signaling pathway KEGG L3 derived feature, a lysine biosynthesis KEGG L3 derived feature, a protein export KEGG L3 derived feature, an arachidonic acid metabolism KEGG L3 derived feature, a thiamine metabolism KEGG L3 derived feature, a phenylpropanoid biosynthesis KEGG L3 derived feature, a ribosome biogenesis KEGG L3 derived feature, a nucleotide excision repair KEGG L3 derived feature, a synthesis and degradation of ketone bodies KEGG L3 derived feature, a benzoate degradation KEGG L3 derived feature, a sulfur metabolism KEGG L3 derived feature, a metabolism of xenobiotics by cytochrome P450 KEGG L3 derived feature, a penicillin and cephalosporin biosynthesis KEGG L3 derived feature, a drug metabolism—cytochrome p450 KEGG L3 derived feature, a purine metabolism KEGG L3 derived feature, a novobiocin biosynthesis KEGG L3 derived feature, a propanoate metabolism KEGG L3 derived feature, a limonene and pinene degradation KEGG L3 derived feature, an aminobenzoate degradation KEGG L3 derived feature, a Huntington's disease KEGG L3 derived feature, a C5-branched dibasic acid metabolism KEGG L3 derived feature, a folate biosynthesis KEGG L3 derived feature, a phenylalanine metabolism KEGG L3 derived feature, and/or any other suitable combination of features.

However, performing the characterization process for in particular dandruff condition and/or any other scalp-related conditions can be performed in any suitable manner using any suitable features.

4.2.D Characterization Process—Pimple-Related Condition

In variations of Block S130, performing a characterization process can be for one or more pimple-related conditions. In particular, pimple-related conditions can include any suitable acne-related conditions.

In variations, a set of features for characterizations of pimple-related and/or other skin-related conditions can include features including and/or otherwise derived from one or more of the following taxa: Lactobacillales, and/or any other suitable taxa.

In relation to Block S130, additionally or alternatively, the set of features associated can include functional diversity features including and/or otherwise derived from one or more of: COG derived features, KEGG L2, L3, L4 derived features, and any other suitable functional diversity features, and/or any other suitable features.

4.2.E Characterization Process—Eczema.

In variations of Block S130, performing a characterization process can be for one or more eczema conditions. In particular eczema can include a skin condition characterized by skin inflammation. In an example eczema can be characterized by non-microbiome-based tests.

In variations, a set of features for characterizations of eczema and/or other skin-related conditions can include features including and/or otherwise derived from one or more of the following taxa: Streptococcaceae, *Streptococcus*, Lactobacillales, *Veillonella*, and/or any other suitable taxa.

In relation to Block S130, additionally or alternatively, the set of features associated can include functional diversity features including and/or otherwise derived from one or more of: COG derived features, KEGG L2, L3, L4 derived features, and any other suitable functional diversity features, and/or any other suitable features.

Thus, characterization of the subject can include characterization of the subject as someone with one or more skin-related conditions based upon detection of one or more of the above features, in a manner that is an alternative or supplemental to typical methods of diagnosis. In variations of the specific example, the set of features can, however, include any other suitable features useful for diagnostics.

4.3 Method—Personalization to a User.

The method 100 can additionally or alternatively include Block S140, which recites: determining a therapy for preventing, ameliorating, and/or otherwise modifying a skin-related condition. Block S140 functions to identify and/or predict therapies (e.g., probiotic-based therapies, phage-based therapies, small molecule-based therapies, etc.) that can shift a user's microbiome composition and/or functional diversity features toward a desired equilibrium state in promotion of the user's health. Block S140 can additionally or alternatively include generating and/or applying a therapy model for determining the therapy. In Block S140, the therapies can be selected from therapies including one or more of: probiotic therapies, prebiotic therapies, antibiotic therapies, antifungal therapies, phage-based therapies, small molecule-based therapies, cognitive/behavioral therapies, physical therapies (e.g., physical rehabilitation, bathing hygiene, daily hygiene, etc.), clinical therapies, medication-based therapies, topical application-based therapies (e.g., salicylic acid, benzoyl peroxide, vitamin A creams, moisturizer, steroid creams, antihistamines, shampoo, lotions, oils, creams, etc.), alternative medicine-based therapies, environmental-based therapies (e.g., light-based therapies, temperature-based therapies, etc.), diet-related therapies, and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in the user can be used to downregulate or otherwise eliminate populations of the certain bacteria. As such, bacteriophage-based therapies can be used to reduce the size(s) of the undesired population(s) of bacteria represented in the user. Complementarily, bacteriophage-based therapies can be used to increase the relative abundances of bacterial populations not targeted by the bacteriophage(s) used. In a variation, Blocks S140 and/or S170 can include automatically initiating a signal that controls a treatment system to promote the therapy (e.g., based on a characterization, a therapy model output, etc.), where initiating the signal can include one or more of: generating and transmitting control instructions to a treatment system (e.g., controlling a probiotic dispensing system to provide a probiotic to a user, etc.), initiating notification provision (e.g., to inform a user regarding one or more characterizations and/or therapies, etc.), and/or any other suitable operation in controlling treatment systems to promote therapies.

Figure 6:
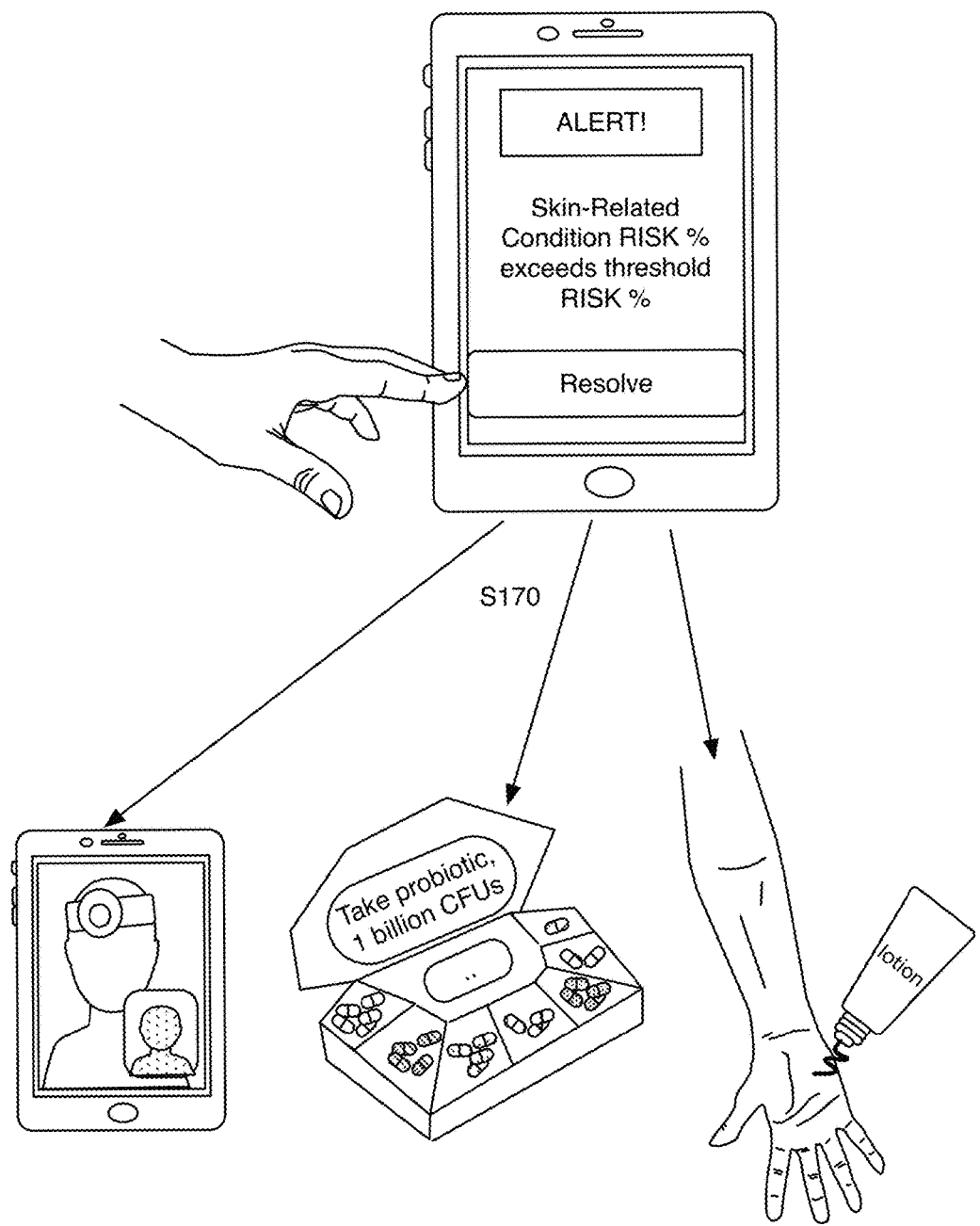
FIG. 6 depicts a variation of promoting therapies in variations of an embodiment of a method for microbiome characterization.

In another specific example, Block S140 can include facilitating an interaction between a user and a care provider (e.g., scheduling an appointment with a care provider; initiating a telemedicine conference over a wireless communication channel, as shown in FIG. 6; etc.), such as in response to and/or concurrently with a trigger condition (e.g., characterizing a skin-related condition risk exceeding a threshold; manual request by a user or care provider; identifying an effectiveness score below a threshold based on analysis of post-therapy biological samples; etc.).

Figure 7:
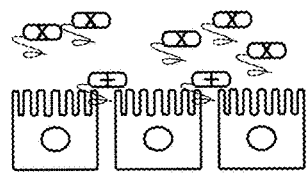
FIG. 7 depicts variations of mechanisms by which probiotic-based therapies operate in an embodiment of a method for microbiome characterization.
Figure 7:
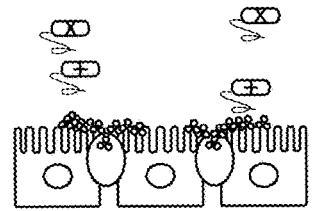
Figure 7:
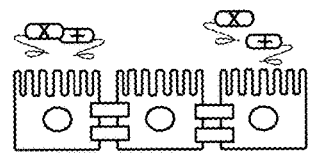
Figure 7:
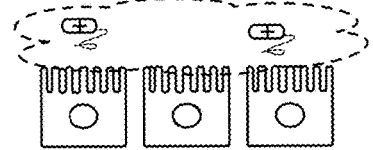
Figure 7:
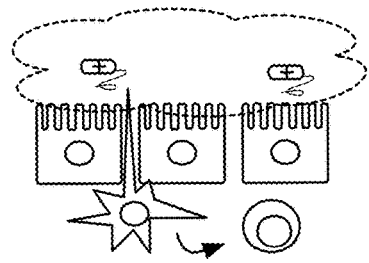
Figure 7:
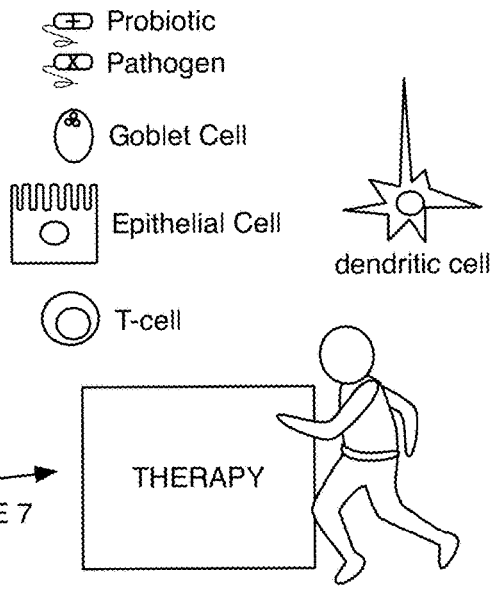

Regarding Block S140, in another specific example of probiotic therapies, as shown in FIG. 7, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a user (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a user's microbiome away from a state of dysbiosis.

In variations, Block S140 can include generating a therapy model based upon data from a large population of users, which can include the population of users from which the microbiome datasets are derived (e.g., in Block S110), where microbiome composition and/or functional features or states of health, prior exposure to and post exposure to a variety of therapeutic measures, are well characterized. Such data can be used to train and validate the therapy provision model, in identifying therapeutic measures that provide desired outcomes for users based upon different microbiome characterizations. Additionally or alternatively, generating (and/or applying) a therapy model can be based on characterizations outputted from one or more characterization models. In variations, therapy models, characterization models, and/or other suitable models can leverage machine learning approaches analogous to those described in U.S. application Ser. No. 15/374,890 filed 9 Dec. 2016, which is herein incorporated in its entirety by this reference. In a variation, generating and/or applying a therapy model can be based on one or more causes for a skin-related condition (e.g., a cause of a skin-related condition risk). For example, the method 100 can include: generating a characterization including a skin-related condition risk (e.g., for any suitable skin-related condition); determining a cause for the skin-related condition risk based on at least one microbiome dataset (e.g., a user microbiome composition feature and a user microbiome functional diversity feature extracted from microbiome datasets); and determining the therapy based on the cause, where the therapy can be operable to reduce the skin-related condition risk. However, therapy models and/or other suitable models (e.g., characterization models) can include any one or more probabilistic properties, heuristic properties, deterministic properties, and/or any other suitable properties, and/or can be configured in any suitable manner.

Regarding Block S140, processing of therapy models can be analogous to processing of characterization models (e.g., described for Block S130), where any number and/or types of treatment models can be generated for different purposes. In a variation, the therapy model can be derived in relation to identification of a "normal" or baseline microbiome composition and/or functional features, as assessed from users of a population of users who are identified to be in good health. Upon identification of a subset of users of the population of users who are characterized to be in good health (e.g., using features of the characterization process), therapies that modulate microbiome compositions and/or functional features toward those of users in good health can be generated in Block S140. Block S140 can thus include identification of one or more baseline microbiome compositions and/or functional features (e.g., one baseline microbiome for each of a set of demographics), and potential therapy formulations and therapy regimens that can shift microbiomes of users who are in a state of dysbiosis toward one of the identified baseline microbiome compositions and/or functional features. The therapy model can, however, be generated and/or refined in any other suitable manner.

In relation to Block S140, microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can include a single type of microorganism that has an acute or moderated effect upon a user's microbiome. Additionally or alternatively, microorganism compositions can include balanced combinations of multiple types of microorganisms that are configured to cooperate with each other in driving a user's microbiome toward a desired state. For instance, a combination of multiple types of bacteria in a probiotic therapy can include a first bacteria type that generates products that are used by a second bacteria type that has a strong effect in positively affecting a user's microbiome. Additionally or alternatively, a combination of multiple types of bacteria in a probiotic therapy can include several bacteria types that produce proteins with the same functions that positively affect a user's microbiome.

Regarding Block S140, probiotic compositions can be naturally or synthetically derived. For instance, in one application, a probiotic composition can be naturally derived from fecal matter or other biological matter (e.g., of one or more users having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli Nissle, Akkermansia muciniphila, Prevotella bryantii*, etc.), gram-positive bacteria (e.g., *Bifidobacterium animalis* (including subspecies *lactis*), *Bifidobacterium longum* (including subspecies *infantis*), *Bifidobacterium bifidum, Bifidobacterium pseudolongum, Bifidobacterium thermophilum, Bifidobacterium breve, Lactobacillus rhamnosus, Lactobacillus acidophilus, Lactobacillus casei, Lactobacillus helveticus, Lactobacillus plantarum, Lactobacillus fermentum, Lactobacillus salivarius, Lactobacillus delbrueckii* (including subspecies *bulgaricus*), *Lactobacillus johnsonii, Lactobacillus reuteri, Lactobacillus gasseri, Lactobacillus brevis* (including subspecies *coagulans*), *Bacillus cereus, Bacillus subtilis* (including var. Natto), *Bacillus polyfermenticus, Bacillus clausii, Bacillus licheniformis, Bacillus coagulans, Bacillus pumilus, Faecalibacterium prausnitzii, Streptococcus thermophiles, Brevibacillus brevis, Lactococcus lactis, Leuconostoc mesenteroides, Enterococcus faecium, Enterococcus faecalis, Enterococcus durans, Clostridium butyricum, Sporolactobacillus inulinus, Sporolactobacillus vineae, Pediococcus acidilactic, Pediococcus pentosaceus,* etc.), and/or any other suitable type of microorganism agent.

In a variation of Block S140, for users who exhibit photosensitivity, dry skin or dandruff and/or other skin-related conditions, a probiotic therapy can include a combination of one or more of: Bacteroidetes (phylum), *Propionibacterium* (genus), *Staphylococcus* (genus), *Corynebacterium* (genus), *Streptococcus* (genus) provided at dosages of 1 million to 10 billion CFUs and/or other suitable CFUs, such as determined from a therapy model that predicts positive adjustment of a patient's microbiome in response to the therapy. In another variation of Block S140, for users who exhibit Eczema and/or other suitable skin-related conditions, a probiotic therapy can include a combination of one or more of: Streptococcaceae, *Streptococcus*, Lactobacillales, *Veillonella* provided at dosages of 1 million to 10 billion CFUs, and/or other suitable CFUs, such as determined from a therapy model that predicts positive adjustment of a patient's microbiome in response to the therapy. In another variation, for users who exhibit dry skin and/or other suitable skin-related conditions, a probiotic therapy can include a combination of one or more microorganisms from: Actinobacteria (class), Actinobacteria (phylum), *Propionibacterium* (genus) provided at dosages of 1 million to to billion CFUs and/or other suitable CFUs, such as determined from a therapy model that predicts positive adjustment of a patient's microbiome in response to the therapy. In another variation, for users who exhibit dandruff and/or other suitable skin-related conditions, a probiotic therapy can include a combination of one or more of: *Roseburia* (genus), *Blautia* (genus), *Bacteroides* (genus), *Pseudobutyrivibrio* (genus), *Alistipes* (genus), *Faecalibacterium* (genus), *Collinsella* (genus), *Clostridium* (genus), *Anaerostipes* (genus), *Dorea* (genus), *Subdoligranulum* (genus), *Sarcina* (genus), *Lachnospira* (genus), *Anaerotruncus* (genus), *Parabacteroides* (genus), *Flavonifractor* (genus), *Intestinibacter* (genus), *Erysipelatoclostridium* (genus), *Phascolarctobacterium* (genus), *Streptococcus* (genus), *Odoribacter* (genus), *Sutterella* (genus), *Corynebacterium* (genus), *Bilophila* (genus), *Terrisporobacter* (genus), *Prevotella* (genus), Porphyromonadaceae (family), Lachnospiraceae (family), Coriobacteriaceae (family), Clostridiaceae (family), Ruminococcaceae (family), Bacteroidaceae (family), Erysipelotrichaceae (family), Rikenellaceae (family), Prevotellaceae (family), Sutterellaceae (family), Flavobacteriaceae (family), Streptococcaceae (family), Veillonellaceae (family), Acidaminococcaceae (family), Desulfovibrionaceae (family), Oscillospiraceae (family), Corynebacteriaceae (family), Pasteurellaceae (family), Bacteroidales (order), Selenomonadales (order), Coriobacteriales (order), Clostridiales (order), Erysipelotrichales (order), Lactobacillales (order), Burkholderiales (order), Flavobacteriales (order), Desulfovibrionales (order), Pasteurellales (order), Bacteroidia (class), Negativicutes (class), Betaproteobacteria (class), Clostridia (class), Erysipelotrichia (class), Flavobacteriia (class), Gammaproteobacteria (class), Bacteroidetes (phylum), Proteobacteria (phylum), Firmicutes (phylum), *Propionibacterium* (genus), *Staphylococcus* (genus) provided at dosages of 1 million to to billion CFUs and/or other suitable CFUs, such as determined from a therapy model that predicts positive adjustment of a patient's microbiome in response to the therapy. In another variation, for users who exhibit Pimples and/or other suitable skin-related conditions, a probiotic therapy can include a combination of one or more of: Lactobacillales provided at dosages of 1 million to 10 billion CFUs and/or other suitable CFUs, such as determined from a therapy model that predicts positive adjustment of a patient's microbiome in response to the therapy.

In specific examples of Block S140, a user can be instructed to ingest capsules including the probiotic formulation according to a regimen tailored to one or more of his/her: physiology (e.g., body mass index, weight, height), demographics (e.g., gender, age), severity of dysbiosis, sensitivity to medications, and any other suitable factor.

Additionally or alternatively, regarding Block S140, therapies promoted by the therapy model of Block S140 can include one or more of: consumables (e.g., food items, beverage items, nutritional supplements), suggested activities (e.g., exercise regimens, adjustments to alcohol consumption, adjustments to cigarette usage, adjustments to drug usage), topical therapies (e.g., lotions, ointments, antiseptics, etc.), adjustments to hygienic product usage (e.g., use of shampoo products, use of conditioner products, use of soaps, use of makeup products, etc.), adjustments to diet (e.g., sugar consumption, fat consumption, salt consumption, acid consumption, etc.), adjustments to sleep behavior, living arrangement adjustments (e.g., adjustments to living with pets, adjustments to living with plants in one's home environment, adjustments to light and temperature in one's home environment, etc.), nutritional supplements (e.g., vitamins, minerals, fiber, fatty acids, amino acids, prebiotics, probiotics, etc.), medications, antibiotics, and any other suitable therapeutic measure. Among the prebiotics suitable for treatment, as either part of any food or as supplement, are included the following components: 1,4-dihydroxy-2-naphthoic acid (DHNA), Inulin, trans-Galactooligosaccharides (GOS), Lactulose, Mannan oligosaccharides (MOS), Fructooligosaccharides (FOS), Neoagaro-oligosaccharides (NAOS), Pyrodextrins, Xylo-oligosaccharides (XOS), Isomalto-oligosaccharides (IMOS), Amylose-resistant starch, Soybean oligosaccharide (SBOS), Lactitol, Lactosucrose (LS), Isomaltulose (including Palatinose), Arabinoxylooligosaccharides (AXOS), Raffinose oligosaccharides (RFO), Arabinoxylans (AX), Polyphenols or any other compound capable of changing the microbiota composition with a desirable effect. In a variation, Blocks S140 and/or S170 can include deriving a therapeutic composition associated with at least one of a microbiome composition and/or functional diversity dataset (e.g., extracted features). For example, the method 100 can include determining a modulator of a biomolecule associated with the skin-related condition (e.g., a modulator of a biomolecule derived from a set of taxa associated with the skin-related condition); deriving a therapeutic composition for the skin-related condition based on the modulator; and promoting the therapeutic composition.

The method 100 can additionally or alternatively include Block S150, which recites: receiving a biological sample from a user. Block S150 functions to facilitate generation of a microbiome dataset for the user that can be used to derive inputs for the characterization process. As such, receiving, processing, and analyzing the biological sample preferably facilitates generation of a microbiome dataset for the user, which can be used to provide inputs for a characterization process. In Block S150, the biological sample is preferably generated from the user and/or an environment of the user in a non-invasive manner (e.g., using a provided sample kit, etc.), but can additionally or alternatively be received in a semi-invasive manner, invasive manner, and/or in any suitable manner.

Furthermore, in Block S150, processing and analyzing the biological sample from the user is preferably performed in a manner similar to that of one of the embodiments, variations, and/or examples of sample processing described in relation to Block S1100 above, and/or in U.S. application Ser. No. 15/452,529 filed 7 Mar. 2017, which is incorporated in its entirety by this reference. However, biological sample reception and processing in Block S150 can alternatively be performed in any other suitable manner.

Figure 3:
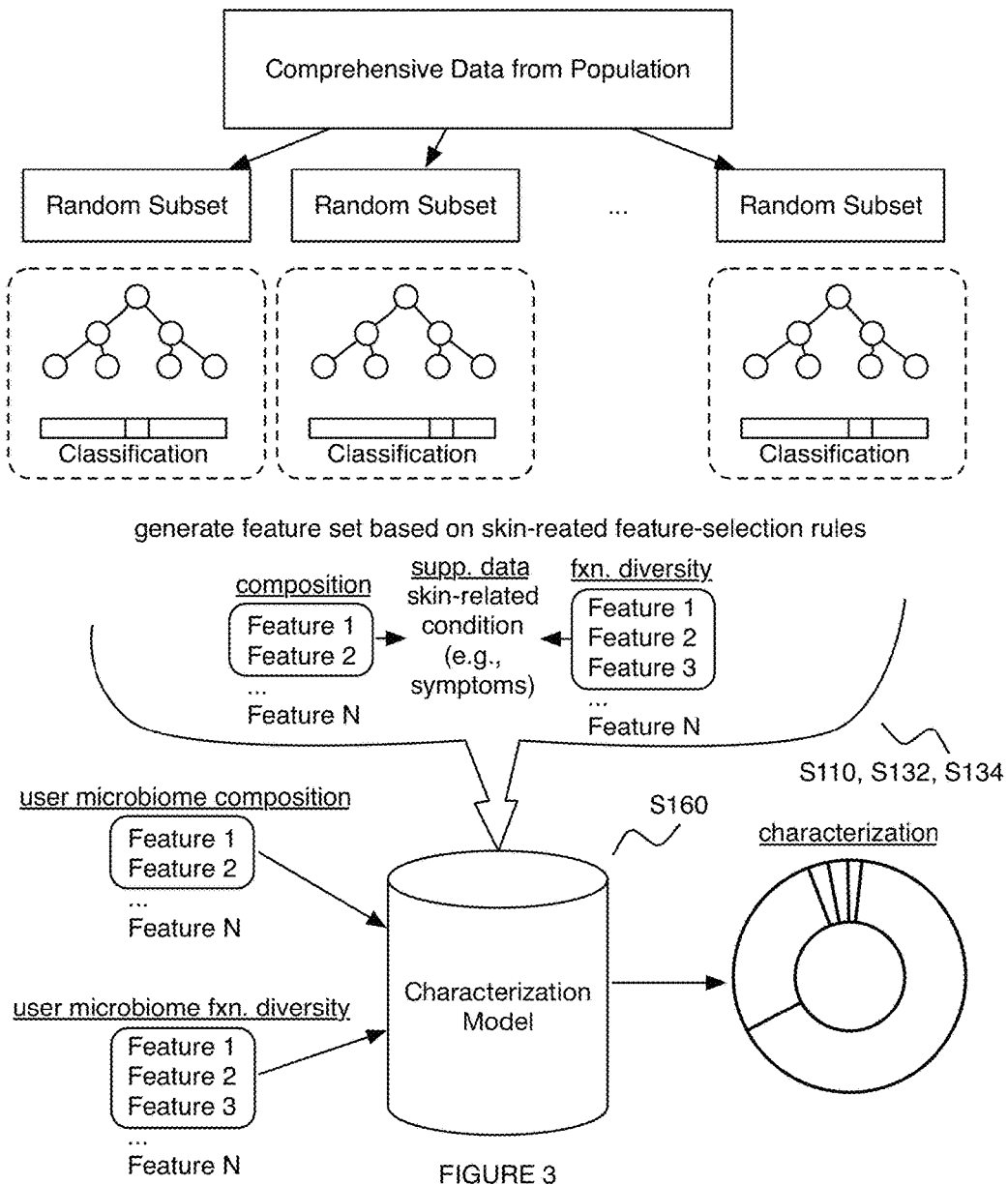
FIG. 3 depicts a schematic representation of a variation of generating and applying a characterization model in an embodiment of a method for microbiome characterization.

As shown in FIG. 3, the method can additionally or alternatively include Block S160, which recites: determining, with the characterization process, a characterization of the user based upon processing a microbiome dataset derived from a biological sample of the user. Block S160 can function to extract features from microbiome-derived data of the user (e.g., based on evaluating the microbiome datasets against computer-implemented rules), and use the features as inputs into an embodiment, variation, or example of the characterization process (e.g., a characterization model) described in Block S130 above. Identifying the characterization in Block S160 thus preferably includes identifying features and/or combinations of features associated with the microbiome composition and/or functional features of the user, inputting the features into the characterization process, and receiving an output that characterizes the user as belonging to one or more of: a behavioral group, a gender group, a dietary group, a disease-state group, and/or any other suitable group capable of being identified by the characterization process. Block S160 can further include generation of and/or output of a confidence metric associated with the characterization of the user. For instance, a confidence metric can be derived from the number of features used to generate the characterization, relative weights or rankings of features used to generate the characterization, measures of bias in the characterization process, and/or any other suitable parameter associated with aspects of the characterization process. In some variations, features extracted from the microbiome dataset of the user can be supplemented with survey-derived and/or medical history-derived features from the user, which can be used to further refine the characterization process of Block S130. However, the microbiome dataset of the user can additionally or alternatively be used in any other suitable manner to enhance the models of the method 100, and Block S160 can be performed in any suitable manner.

4.4 Method—Promoting and Monitoring a Therapy.

Figure 8:
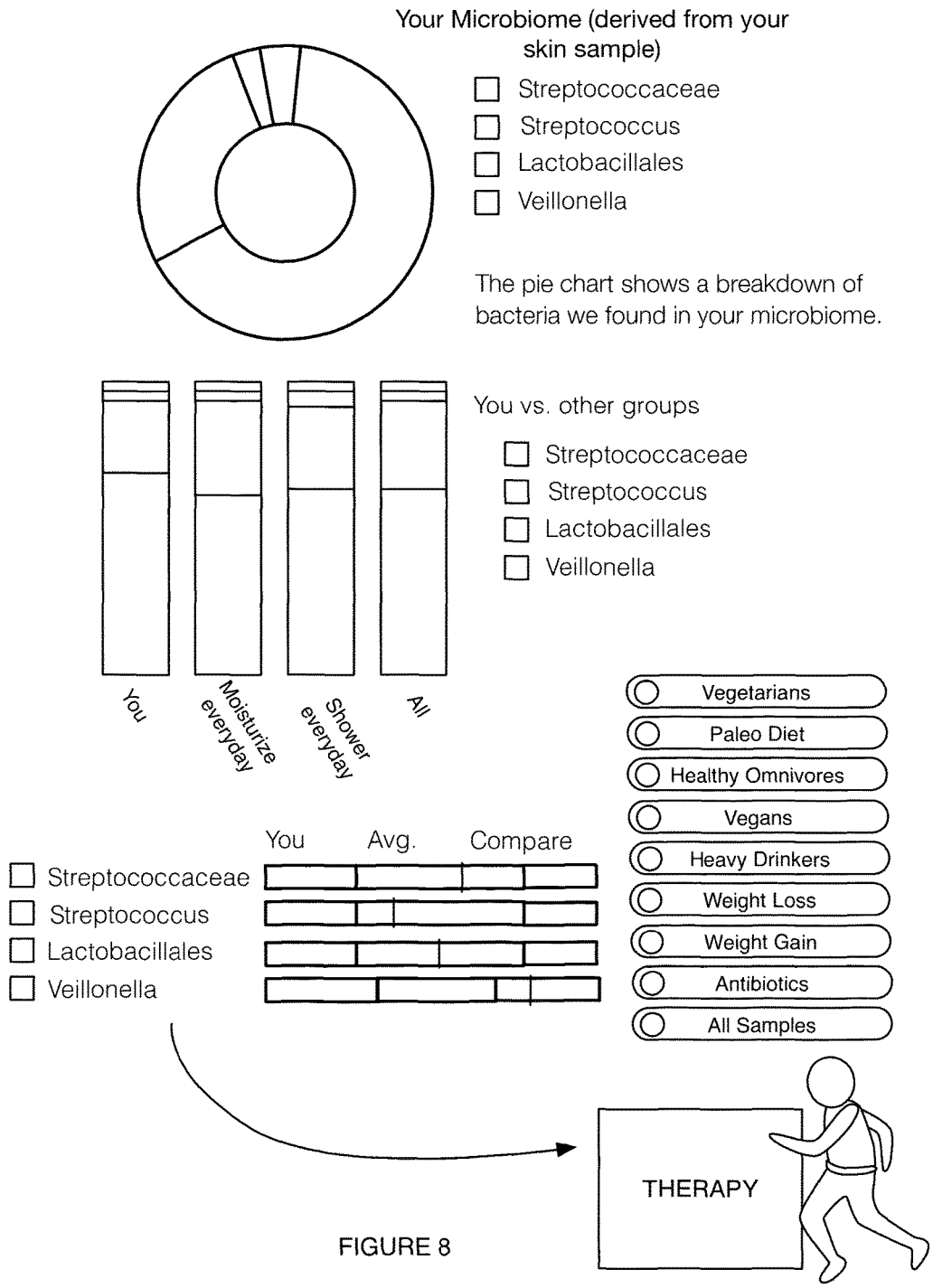
FIG. 8 depicts a variation of notification provision in an embodiment of a method for microbiome characterization.

As shown in FIG. 6, the method 100 can additionally or alternatively include Block S170, which recites: promoting a therapy for the skin-related condition to the user (e.g., based upon the characterization, a therapy model, etc.). Block S170 functions to determine, recommend, and/or provide a personalized therapy to the user, in order to shift the microbiome composition and/or functional features of the user toward a desired equilibrium state. Block S170 can include provision of a customized therapy to the user according to their microbiome composition and functional features, as shown in FIG. 8, where the customized therapy is a formulation of microorganisms configured to correct dysbiosis characteristic of users having the identified characterization. As such, outputs of Block S140 can be used to directly promote a customized therapy formulation and regimen (e.g., dosage, usage instructions) to the user based upon a trained therapy model. Additionally or alternatively, therapy provision can include recommendation of available therapeutic measures configured to shift microbiome composition and/or functional features toward a desired state. In variations, available therapeutic measures can include one or more of: consumables (e.g., food items, beverage items, etc.), topical therapies (e.g., lotions, ointments, antiseptics, etc.), nutritional supplements (e.g., vitamins, minerals, fiber, fatty acids, amino acids, prebiotics, etc.), medications, antibiotics, bacteriophages, and any other suitable therapeutic measure. For instance, a combination of commercially available probiotic supplements can include a suitable probiotic therapy for the user according to an output of the therapy model.

Additionally or alternatively, in a specific example, the therapy of Block S170 can include a bacteriophage-based therapy. In more detail, one or more populations (e.g., in terms of colony forming units) of bacteriophages specific to a certain bacteria (or other microorganism) represented in the user can be used to down-regulate or otherwise eliminate populations of the certain bacteria. As such, bacteriophage-based therapies can be used to reduce the size(s) of the undesired population(s) of bacteria represented in the user. Complementarily, bacteriophage-based therapies can be used to increase the relative abundances of bacterial populations not targeted by the bacteriophage(s) used.

Therapy provision in Block S170 can include provision of notifications to a user regarding the recommended therapy and/or other forms of therapy. Types of notifications and manners of providing notifications can be analogous to that described in U.S. application Ser. No. 15/374,890 filed 9 Dec. 2016, which is incorporated in its entirety by this reference.

Figure 4:
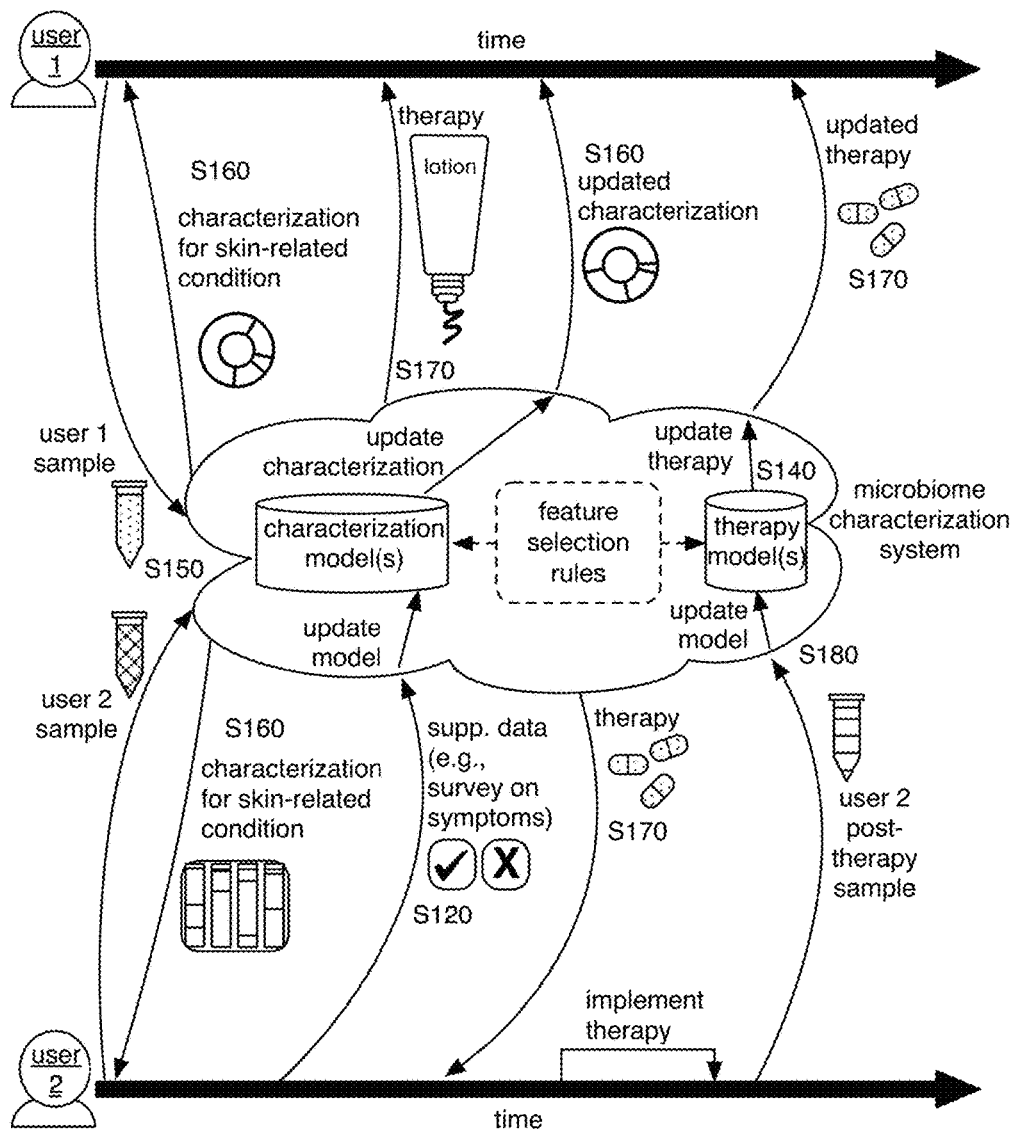
FIG. 4 depicts a variation of applying and updating a characterization model and a therapy model in an embodiment of a method for microbiome characterization.

As shown in FIG. 4, the method 100 can additionally or alternatively include Block S180, which recites: monitoring effectiveness of the therapy for the user, based upon processing biological samples, to assess microbiome composition and/or functional diversity for the user over time. Block S180 functions to gather additional data regarding positive effects, negative effects, and/or lack of effectiveness of a probiotic therapy suggested by the therapy model for users of a given characterization, where the additional data can be used, for example, to generate, update, and/or execute one or more characterization models, therapy models, and/or other suitable models. For example, the method 100 can include updating a model (e.g., characterization model, therapy model, etc.) based one or more of a user microbiome composition dataset (e.g., features extracted from the dataset, etc.), a user microbiome functional diversity dataset (e.g., features extracted from the dataset, etc.), and/or other suitable dataset (e.g., updating a model based on modulation of the skin-related condition, determined based on comparisons of pre-therapy and post-therapy microbiome datasets); and in response to updating the model, determining an update (e.g., to a characterization, to a therapy, etc.) for a second user in relation to the skin-related condition, based on the updated model. In another example, the method 100 can include: receiving a post-therapy biological sample from the user (e.g., after promoting the therapy); generating a post-therapy characterization of the user in relation to the skin-related condition based on the post-therapy biological sample (e.g., post-therapy microbiome composition and/or functional diversity features extracted from the post-therapy biological sample using skin-related feature-selection rules, where the features can be used with a characterization model, etc.); characterizing modulation of the skin-related condition in relation to the user based on the post-therapy characterization (e.g., and one or more pre-therapy characterizations for the user, for a second user, etc.). However, any suitable portion of the method 100 and/or any suitable operation can be performed in response to updating of models. Monitoring of a user during the course of a therapy promoted by the therapy model (e.g., by receiving and analyzing biological samples from the user throughout therapy, by receiving survey-derived data from the user throughout therapy) can thus be used to generate a therapy-effectiveness model for each characterization provided by the characterization process of Block S130, and each recommended therapy measure provided in Blocks S140 and S170.

In Block S180, the user can be prompted to provide additional biological samples at one or more key time points of a therapy regimen that incorporates the therapy, and the additional biological sample(s) can be processed and analyzed (e.g., in a manner similar to that described in relation to Block S120) to generate metrics characterizing modulation of the user's microbiome composition and/or functional features. For instance, metrics related to one or more of: a change in relative abundance of one or more taxonomic groups represented in the user's microbiome at an earlier time point, a change in representation of a specific taxonomic group of the user's microbiome, a ratio between abundance of a first taxonomic group of bacteria and abundance of a second taxonomic group of bacteria of the user's microbiome, a change in relative abundance of one or more functional families in a user's microbiome, and any other suitable metrics can be used to assess therapy effectiveness from changes in microbiome composition and/or functional features. Additionally or alternatively, survey-derived data from the user, pertaining to experiences of the user while on the therapy (e.g., experienced side effects, personal assessment of improvement, etc.) can be used to determine effectiveness of the therapy in Block S180. However, monitoring effectiveness of one or more therapies can be performed in any suitable manner.

The method 100 can, however, include any other suitable blocks or steps configured to facilitate reception of biological samples from users, processing of biological samples from users, analyzing data derived from biological samples, and generating models that can be used to provide customized diagnostics and/or probiotic-based therapeutics according to specific microbiome compositions and/or functional features of users.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The embodiments include every combination and permutation of the various system components and the various method processes, including any variations, examples, and specific examples.

As a person skilled in the art will recognize from the previous detailed description and from the figures and claims, modifications and changes can be made to the embodiments of the invention without departing from the scope of this invention as defined in the following claims.

We claim:

1. A system for evaluating a skin-related condition in relation to a user, the system comprising:
    a handling network operable to collect containers comprising material from a set of users, the handling network comprising:
        a library preparation system operable to fragment and perform multiplex amplification on the material using a primer compatible with a genetic target associated with the skin-related condition;
        a sequencing system operable to determine microorganism sequences from sequencing the material;
    a microbiome characterization system operable to:
        determine microbiome composition data and microbiome functional diversity data based on an alignment between the microorganism sequences and reference sequences associated with the skin-related condition,
        collect supplementary data associated with the skin-related condition for the set of users, and
        transform the supplementary data and features extracted from the microbiome composition data and the microbiome functional diversity data into a characterization model for the skin-related condition; and
    a treatment system operable to provide a treatment to the user for the skin-related condition based on characterizing the user with the characterization model in relation to the skin-related condition.

2. The system of claim 1, wherein the microbiome characterization system is further operable to:
    obtain a set of skin-related feature-selection rules correlating the skin-related condition to a subset of microbiome composition features and a subset of microbiome functional diversity features; and
    generate the features based on evaluating the microbiome composition data and the microbiome functional diversity data against the set of skin-related feature-selection rules, wherein the set of skin-related feature-selection rules are operable to improve the microbiome characterization system by facilitating decreased processing time to transform the supplementary data and the features into the characterization model.

3. The system of claim 2, wherein the microbiome functional diversity features comprises at least one of: a cluster of orthologous group of proteins feature, a genomic functional feature, a taxonomic feature, a chemical functional feature, and a systemic functional feature.

4. The system of claim 1, wherein the handling network further comprises a library preparation system operable to fragment and perform multiplex amplification on the material using a primer compatible with a genetic target associated with the skin-related condition.

5. The system of claim 1, further comprising an interface operable to improve display of skin-related condition information derived from the characterization model, wherein the skin-related condition information comprises a microbiome composition for the user relative to a user group sharing a demographic characteristic, and wherein the microbiome composition comprises a set of taxa comprising at least one of: *Marvinbryantia* (genus), Erysipelotrichales (order), Erysipelotrichia (class), Bacteroidetes (phylum), *Staphylococcus* (genus), Staphylococcaceae (family), Bacillales (order), Actinobacteria (class), Firmicutes (phylum), Actinobacteria (phylum), and *Propionibacterium* (genus).

6. The system of claim 5, wherein the skin-related condition information comprises a change in the microbiome composition over time and a change in a microbiome functional diversity over time in relation to the treatment and the skin-related condition.

7. The system of claim 1, wherein the features comprise at least one of a Kyoto Encyclopedia of Genes and Genomes (KEGG) functional feature and a Clusters of Orthologous Groups (COG) functional feature, and wherein the features comprise transformation microbiome features derived from at least one of: a relative abundance monotonic transformation and a non-monotonic transformation.

8. The system of claim 7, wherein the transformation microbiome features are associated with at least one of: a normalization, a feature vector derived at least one of linear latent variable analysis and non-linear latent variable analysis, linear regression, non-linear regression, a kernel method, a feature embedding method, machine learning, and a statistical inference method.

9. The system of claim 7, wherein the skin-related condition comprises dry skin, and wherein the features comprise a microbiome composition feature associated with a relative abundance of at least one of: *Staphylococcus* (genus), Staphylococcaceae (family), Bacillales (order), Actinobacteria (class), Firmicutes (phylum), Actinobacteria (phylum), and *Propionibacterium* (genus).

10. A method for characterizing a skin-related condition in relation to a first user, the method comprising:
    generating a microbiome composition dataset and a microbiome functional diversity dataset based on microorganism sequences derived from biological samples from a set of users, wherein generating the microbiome composition dataset and the microbiome functional diversity dataset comprises:
        identifying primers for nucleic acid sequences associated with the skin-related condition,
        fragmenting nucleic acid material,
        amplifying the fragmented nucleic acid material using the identified primers, and
        determining an alignment of the microorganism sequences to reference sequences associated with the skin-related condition;
    receiving a supplementary dataset informative of the skin-related condition for the set of users;
    obtaining a set of skin-related feature-selection rules correlating the skin-related condition to a subset of microbiome composition features and a subset of microbiome functional diversity features;
    generating a feature set based on evaluating the microbiome composition dataset and the microbiome functional diversity dataset against the set of skin-related feature-selection rules;
    applying the feature set with the supplementary dataset to generate a characterization model for the skin-related condition;
    generating a first characterization of the first user in relation to the skin-related condition using the characterization model; and providing a therapy to the first user for the skin-related condition based on the first characterization.

11. The method of claim 10, wherein the characterization model is an eczema-related characterization model, the method further comprising:
generating a second feature set based on the microbiome composition dataset and the microbiome functional diversity dataset;
applying the second feature set to generate a scalp-related characterization model; and
generating a second characterization of the first user in relation to a scalp-related condition using the scalp-related characterization model.

12. The method of claim 11, further comprising:
generating a third characterization of the first user in relation to a dry skin-related condition using a dry skin-related characterization model;
wherein promoting the therapy to the first user comprises promoting the therapy based on the first, second, and third characterizations.

13. The method of claim 10, wherein promoting the therapy comprises automatically initiating a signal that controls a treatment system to promote the therapy based on the first characterization of the first user in relation to the skin-related condition.

14. The method of claim 11, further comprising:
generating a user microbiome composition feature for the first user based on a first skin-related feature-selection rule of the set of skin-related feature-selection rules; and
generating a user microbiome functional feature for the first user based on a second skin-related feature-selection rule of the set of skin-related feature-selection rules, wherein the first and the second skin-related feature-selection rules improve the characterization model, and
wherein generating the first characterization comprises generating the first characterization based on the user microbiome composition feature, the user microbiome functional feature, and characterization model.

15. The method of claim 14,
wherein the first characterization comprises a skin-related condition risk comprising at least one of an eczema risk, a dry skin risk, a scalp-related condition risk, a photosensitivity risk, and an acne risk, and the method further comprising:
determining a cause for the skin-related condition risk based on the user microbiome composition feature and the user microbiome functional feature; and
determining the therapy based on the cause, wherein the therapy is operable to reduce the skin-related condition risk.

16. The method of claim 14, further comprising:
updating the characterization model based on the user microbiome composition feature and the user microbiome functional feature; and
in response to updating the characterization model, updating a second characterization for a second user in relation to the skin-related condition based on the updated characterization model.

17. The method of claim 10, further comprising:
after promoting the therapy, receiving a post-therapy biological sample from the first user;
generating a post-therapy characterization of the first user in relation to the skin-related condition based on the characterization model and the post-therapy biological sample; and
characterizing modulation of the skin-related condition in relation to the first user based on the post-therapy characterization and the characterization.

18. The method of claim 17,
wherein the therapy is operable to facilitate modification of a microbiome composition and a microbiome functional diversity of the first user, and the method further comprising:
determining post-therapy user microbiome composition features and post-therapy microbiome functional diversity features based on the post-therapy biological sample and the set of skin-related feature-selection rules, wherein the post-therapy user microbiome composition features are associated with the subset of microbiome composition features, wherein the post-therapy microbiome functional diversity features are associated with the subset of microbiome functional diversity features, and
wherein generating the post-therapy characterization comprises generating the post-therapy characterization based on the post-therapy user microbiome composition features, the post-therapy microbiome functional diversity features, and the characterization model.

19. The method of claim 18, wherein the therapy is selected based on a therapy model, the method further comprising:
updating the therapy model based on the modulation of the skin-related condition in relation to the first user;
in response to updating the therapy model, updating a second therapy for a second user based on the updated therapy model; and
promoting the updated second therapy to the second user for the skin-related condition.

20. The method of claim 10, further comprising:
identifying a primer compatible with a genetic target associated with the skin-related condition, wherein identifying a primer compatible with a genetic target associated with the skin-related condition comprises identifying the primer based on the set of skin-related feature-selection rules;
amplifying nucleic acid material using the identified primer and a user biological sample from the first user; and
sequencing the nucleic acid material to determine user microorganism sequences,
wherein generating the first characterization for the first user comprises generating the first characterization based on the characterization model and the user microorganism sequences.

21. The method of claim 10, wherein the skin-related condition comprises Eczema, and wherein the subset of microbiome composition features comprises a composition feature associated with a set of taxa comprising at least one of: Streptococcaceae, *Streptococcus*, Lactobacillales, and *Veillonella*.

22. The method of claim 21, further comprising:
determining a modulator of a biomolecule associated with the set of taxa and the skin-related condition; and
deriving a therapeutic composition for the skin-related condition based on the modulator,
wherein promoting the therapy comprises providing the therapeutic composition to the first user based on the characterization.

23. The method of claim 21, wherein the composition feature for a single microorganism is associated with at least one of the following metrics: relative abundance, differential relative abundance, presence, and absence.

24. The method of claim 10, wherein the skin-related condition comprises a scalp-related condition including dandruff, and wherein the subset of microbiome composition features comprises a variety of features associated with a set of taxa comprising and including at least one of: *Propionibacterium* sp. MSP09A (species), *Bacteroides vulgatus* (species, *Streptococcus* sp. BS35a (species), *Staphylococcus* sp. C9I2 (species), *Phascolarctobacterium* sp. 377 (species), *Faecalibacterium prausnitzii* (species), *Alistipes putredinis* (species), *Alistipes* sp. EBA6-25cl2 (species), *Alistipes* sp. RMA 9912 (species) *Anaerostipes* sp. 5_1_63FA (species), *Bacteroides acidifaciens* (species), *Bacteroides caccae* (species), *Bacteroides fragilis* (species), *Bacteroides plebeius* (species), *Bacteroides* sp. AR20 (species), *Bacteroides* sp. AR29 (species), *Bacteroides* sp. D22 (species), *Bacteroides* sp. DJF (species), *Bacteroides* sp. SLC1-38 (species), *Bacteroides* sp. XB12B (species), *Bacteroides vulgatus* (species), *Blautia faecis* (species), *Blautia luti* (species), *Blautia* sp. YHC-4 (species), *Blautia stercoris* (species), *Blautia wexlerae* (species), *Collinsella aerofaciens* (species), *Corynebacterium* sp. (species), *Corynebacterium spheniscorum* (species), *Corynebacterium ulcerans* (species), *Dorea formicigenerans* (species), *Dorea longicatena* (species), *Lachnospira pectinoschiza* (species), *Odoribacter splanchnicus* (species), *Parabacteroides distasonis* (species), *Parabacteroides merdae* (species), *Phascolarctobacterium faecium* (species), *Propionibacterium acnes* (species), *Propionibacterium granulosum* (species), *Propionibacterium* sp. MSP09A (species), *Roseburia intestinalis* (species), *Roseburia inulinivorans* (species), *Roseburia* sp. 11SE39 (species), *Staphylococcus* sp. C9I2 (species), *Staphylococcus* sp. WB18-16 (species), *Streptococcus* sp. BS35a (species), *Streptococcus* sp. oral taxon G59 (species), *Streptococcus thermophilus* (species), *Subdoligranulum variabile* (species), *Sutterella stercoricanis* (species), *Sutterella wadsworthensis Propionibacterium* (genus), *Staphylococcus* (genus), *Roseburia* (genus), *Blautia* (genus), *Bacteroides* (genus), *Pseudobutyrivibrio* (genus), *Alistipes* (genus), *Faecalibacterium* (genus), *Collinsella* (genus), *Clostridium* (genus), *Anaerostipes* (genus), *Dorea* (genus), *Subdoligranulum* (genus), *Sarcina* (genus), *Lachnospira* (genus), *Anaerotruncus* (genus), *Parabacteroides* (genus), *Flavonifractor* (genus), *Intestinibacter* (genus), *Erysipelatoclostridium* (genus), *Phascolarctobacterium* (genus), *Streptococcus* (genus), *Odoribacter* (genus), *Sutterella* (genus), *Bifidobacterium* (genus), *Corynebacterium* (genus), *Bilophila* (genus), *Terrisporobacter* (genus), *Dialister* (genus), *Prevotella* (genus), *Marvinbryantia* (genus), Propionibacteriaceae (family), Staphylococcaceae (family), Porphyromonadaceae (family), Lachnospiraceae (family), Peptostreptococcaceae (family), Coriobacteriaceae (family), Clostridiaceae (family), Ruminococcaceae (family), Bacteroidaceae (family), Erysipelotrichaceae (family), Rikenellaceae (family), Prevotellaceae (family), Sutterellaceae (family), Flavobacteriaceae (family), Streptococcaceae (family), Veillonellaceae (family), Acidaminococcaceae (family), Desulfovibrionaceae (family), Oscillospiraceae (family), Bifidobacteriaceae (family), Corynebacteriaceae (family), Pasteurellaceae (family), Bacteroidales (order), Actinomycetales (order), Selenomonadales (order), Bacillales (order), Coriobacteriales (order), Clostridiales (order), Erysipelotrichales (order), Lactobacillales (order), Burkholderiales (order), Flavobacteriales (order), Desulfovibrionales (order), Bifidobacteriales (order), Pasteurellales (order), Actinobacteria (class), Bacteroidia (class), Negativicutes (class), Betaproteobacteria (class), Clostridia (class), Erysipelotrichia (class), Flavobacteriia (class), Bacilli (class), Deltaproteobacteria (class), Gammaproteobacteria (class), Bacteroidetes (phylum), Actinobacteria (phylum), Proteobacteria (phylum), Firmicutes (phylum), and Verrucomicrobia (phylum).

25. The method of claim 24, wherein the subset of microbiome functional diversity features comprises a Kyoto Encyclopedia of Genes and Genomes (KEGG) functional features associated with at least one of: a glycan biosynthesis and metabolism KEGG L2 derived feature, an environmental adaptation KEGG L2 derived feature, a cancers KEGG L2 derived feature, an immune system diseases KEGG L2 derived feature, a transcription KEGG L2 derived feature, a signaling molecules and interaction KEGG L2 derived feature, a membrane transport KEGG L2 derived feature, a cell motility KEGG L2 derived feature, a cellular processes and signaling KEGG L2 derived feature, a metabolism of cofactors and vitamins KEGG L2 derived feature, a metabolism KEGG L2 derived feature, a neurodegenerative diseases KEGG L2 derived feature, a metabolic diseases KEGG L2 derived feature, an enzyme families KEGG L2 derived feature, a cell growth and death KEGG L2 derived feature, a carbohydrate metabolism KEGG L2 derived feature, a transport and catabolism KEGG L2 derived feature, a genetic information processing KEGG L2 derived feature, a replication and repair KEGG L2 derived feature, an energy metabolism KEGG L2 derived feature, a digestive system KEGG L2 derived feature, an amino acid metabolism KEGG L2 derived feature, a metabolism of other amino acids KEGG L2 derived feature, a biosynthesis of other secondary metabolites KEGG L2 derived feature, a folding, sorting and degradation KEGG L2 derived feature, a lipid metabolism KEGG L2 derived feature, an infectious diseases KEGG L2 derived feature, a nucleotide metabolism KEGG L2 derived feature, a metabolism of terpenoids and polyketides KEGG L2 derived feature, a renal cell carcinoma KEGG L3 derived feature, an ubiquinone and other terpenoid-quinone biosynthesis KEGG L3 derived feature, an amyotrophic lateral sclerosis KEGG L3 derived feature, a lipoic acid metabolism KEGG L3 derived feature, a cyanoamino acid metabolism KEGG L3 derived feature, a glutathione metabolism KEGG L3 derived feature, a toluene degradation KEGG L3 derived feature, a riboflavin metabolism KEGG L3 derived feature, a plant-pathogen interaction KEGG L3 derived feature, a prenyltransferases KEGG L3 derived feature, a biosynthesis of ansamycins KEGG L3 derived feature, an ABC transporters KEGG L3 derived feature, an inositol phosphate metabolism KEGG L3 derived feature, a citrate cycle (TCA cycle) KEGG L3 derived feature, a chromosome KEGG L3 derived feature, a glycolysis/gluconeogenesis KEGG L3 derived feature, a valine, leucine and isoleucine degradation KEGG L3 derived feature, a primary immunodeficiency KEGG L3 derived feature, a DNA replication proteins KEGG L3 derived feature, a cytoskeleton proteins KEGG L3 derived feature, a peroxisome KEGG L3 derived feature, a transcription machinery KEGG L3 derived feature, a protein folding and associated processing KEGG L3 derived feature, a d-alanine metabolism KEGG L3 derived feature, a translation proteins KEGG L3 derived feature, a glycine, serine and threonine metabolism KEGG L3 derived feature, a lipopolysaccharide biosynthesis proteins KEGG L3 derived feature, an energy metabolism KEGG L3 derived feature, a lipid metabolism KEGG L3 derived feature, a peptidases KEGG L3 derived feature, a carbohydrate digestion and absorption KEGG L3 derived feature, a caprolactam degradation KEGG L3 derived feature, a glycerolipid metabolism KEGG L3 derived feature, a carbon fixation in photosynthetic organisms KEGG L3 derived feature, a membrane and intracellular structural molecules KEGG L3 derived feature, a fatty acid biosynthesis KEGG L3 derived feature, a type I diabetes mellitus KEGG L3 derived feature, a phosphotransferase system (pts) KEGG L3 derived feature, a base excision repair KEGG L3 derived feature, a sporulation KEGG L3 derived feature, a transporters KEGG L3 derived feature, a protein kinases KEGG L3 derived feature, a pantothenate and CoA biosynthesis KEGG L3 derived feature, a cell cycle—Caulobacter KEGG L3 derived feature, a butirosin and neomycin biosynthesis KEGG L3 derived feature, a mismatch repair KEGG L3 derived feature, a pores ion channels KEGG L3 derived feature, an oxidative phosphorylation KEGG L3 derived feature, a cell division KEGG L3 derived feature, a replication, recombination and repair proteins KEGG L3 derived feature, a bacterial motility proteins KEGG L3 derived feature, a carbon fixation pathways in prokaryotes KEGG L3 derived feature, a transcription factors KEGG L3 derived feature, a vitamin b6 metabolism KEGG L3 derived feature, a chloroalkane and chloroalkene degradation KEGG L3 derived feature, a peptidoglycan biosynthesis KEGG L3 derived feature, a drug metabolism—other enzymes KEGG L3 derived feature, a proteasome KEGG L3 derived feature, a RNA transport KEGG L3 derived feature, an ascorbate and aldarate metabolism KEGG L3 derived feature, a cysteine and methionine metabolism KEGG L3 derived feature, a galactose metabolism KEGG L3 derived feature, a tetracycline biosynthesis KEGG L3 derived feature, a translation factors KEGG L3 derived feature, a glycerophospholipid metabolism KEGG L3 derived feature, a pentose phosphate pathway KEGG L3 derived feature, a tyrosine metabolism KEGG L3 derived feature, a photosynthesis proteins KEGG L3 derived feature, a *Vibrio cholerae* pathogenic cycle KEGG L3 derived feature, an amino sugar and nucleotide sugar metabolism KEGG L3 derived feature, a bacterial chemotaxis KEGG L3 derived feature, a tryptophan metabolism KEGG L3 derived feature, a nicotinate and nicotinamide metabolism KEGG L3 derived feature, a histidine metabolism KEGG L3 derived feature, a biotin metabolism KEGG L3 derived feature, a secretion system KEGG L3 derived feature, a cellular antigens KEGG L3 derived feature, a sulfur relay system KEGG L3 derived feature, a taurine and hypotaurine metabolism KEGG L3 derived feature, a photosynthesis KEGG L3 derived feature, a zeatin biosynthesis KEGG L3 derived feature, a methane metabolism KEGG L3 derived feature, a RNA degradation KEGG L3 derived feature, a phosphatidylinositol signaling system KEGG L3 derived feature, a glyoxylate and dicarboxylate metabolism KEGG L3 derived feature, an adipocytokine signaling pathway KEGG L3 derived feature, a starch and sucrose metabolism KEGG L3 derived feature, a chaperones and folding catalysts KEGG L3 derived feature, a vitamin metabolism KEGG L3 derived feature, a pyruvate metabolism KEGG L3 derived feature, a porphyrin and chlorophyll metabolism KEGG L3 derived feature, a geraniol degradation KEGG L3 derived feature, a tuberculosis KEGG L3 derived feature, a tropane, piperidine and pyridine alkaloid biosynthesis KEGG L3 derived feature, a beta-alanine metabolism KEGG L3 derived feature, a PPAR signaling pathway KEGG L3 derived feature, a lysine biosynthesis KEGG L3 derived feature, a protein export KEGG L3 derived feature, an arachidonic acid metabolism KEGG L3 derived feature, a thiamine metabolism KEGG L3 derived feature, a phenylpropanoid biosynthesis KEGG L3 derived feature, a ribosome biogenesis KEGG L3 derived feature, a nucleotide excision repair KEGG L3 derived feature, a synthesis and degradation of ketone bodies KEGG L3 derived feature, a benzoate degradation KEGG L3 derived feature, a sulfur metabolism KEGG L3 derived feature, a metabolism of xenobiotics by cytochrome p450 KEGG L3 derived feature, a penicillin and cephalosporin biosynthesis KEGG L3 derived feature, a drug metabolism—cytochrome p450 KEGG L3 derived feature, a purine metabolism KEGG L3 derived feature, a novobiocin biosynthesis KEGG L3 derived feature, a propanoate metabolism KEGG L3 derived feature, a limonene and pinene degradation KEGG L3 derived feature, an aminobenzoate degradation KEGG L3 derived feature, a Huntington's disease KEGG L3 derived feature, a C5-branched dibasic acid metabolism KEGG L3 derived feature, a folate biosynthesis KEGG L3 derived feature, and a phenylalanine metabolism KEGG L3 derived feature.

26. The method of claim 10, wherein the skin-related condition comprises dry skin, and wherein the subset of microbiome composition features comprises a composition feature associated with a set of taxa including at least one of: *Staphylococcus* (genus), Staphylococcaceae (family), Bacillales (order), Actinobacteria (class), Firmicutes (phylum), Actinobacteria (phylum), and *Propionibacterium* (genus).

27. The method of claim 26, wherein the subset of microbiome functional diversity features comprises at least one of a Kyoto Encyclopedia of Genes and Genomes (KEGG) functional feature and a Clusters of Orthologous Groups (COG) functional feature.

28. The method of claim 10, wherein the skin-related condition comprises photosensitivity, and wherein the subset of microbiome composition features comprises a composition feature associated with a set of taxa comprising at least one of: *Marvinbryantia* (genus), Erysipelotrichales (order), Erysipelotrichia (class), and Bacteroidetes (phylum).

29. The method of claim 28, wherein the subset of microbiome functional diversity features comprises an infectious diseases KEGG L2 derived feature.

30. The method of claim 10, wherein the skin-related condition comprises a pimple-related condition, and wherein the subset of microbiome composition features comprises a composition feature associated with a set of taxa comprising Lactobacillales.

* * * * *